(12) United States Patent
He

(10) Patent No.: US 8,318,207 B2
(45) Date of Patent: Nov. 27, 2012

(54) ENCAPSULATION AND CONTROLLED RELEASE OF SMALL MOLECULES FOR INTRACELLULAR DELIVERY USING THERMALLY RESPONSIVE NANOCAPSULES

(75) Inventor: Xiaoming He, Lexington, SC (US)

(73) Assignee: University of South Carolina, Columbia, SC (US)

( * ) Notice: Subject to any disclaimer, the term of this patent is extended or adjusted under 35 U.S.C. 154(b) by 59 days.

(21) Appl. No.: 12/705,072

(22) Filed: Feb. 12, 2010

(65) Prior Publication Data

US 2010/0203148 A1 Aug. 12, 2010

Related U.S. Application Data

(60) Provisional application No. 61/207,485, filed on Feb. 12, 2009.

(51) Int. Cl.
*A61K 9/14* (2006.01)
(52) U.S. Cl. ........ 424/489; 525/916; 525/917; 977/702; 977/916
(58) Field of Classification Search .................. None
See application file for complete search history.

(56) References Cited

U.S. PATENT DOCUMENTS

2005/0277739 A1* 12/2005 Yang et al. .................... 525/242

OTHER PUBLICATIONS

SH Choi, SH Lee, TG Park. "Temperature-Sensitive Pluronic/Poly(ethylenimine) Nanocapsules for Thermally Triggered Disruption of Intracellular Endosomal Compartment." Biomacromolecules, vol. 7, 2006, pp. 1864-1870.*
JE Chung, M Yokoyama, M Yamato, T Aoyagi, Y Sakurai, T Okano. "Thermo-responsive drug delivery from polymeric micelles constructed using block copolymers of poly(N-isopropylacrylamide) and poly(butylmethacrylate)." Journal of Controlled Release, vol. 62, 1999, pp. 115-127.*
R Dinarvand, A D'Emanuele. "The use of thermoresponsive hydrogels for on-off release of molecules." Journal of Controlled Release, vol. 36, 1995, pp. 221-227.*
"Analog", See Chemicool Periodic Table, Nov. 14, 2011 <http://www.chemicool.com/definition/analog.html>.
"Homolog", See Chemicool Periodic Table, Nov. 14, 2001 <http://www.chemicool.com/definition/homolog.html>.
Chao et al., "Pre-treatment inflammation induced by TNF-alpha augments cryosurgical injury on human prostate cancer", Cryobiology, Aug. 2004, vol. 49, No. 1, pp. 10-27.
Clarke et al., "Chemo-cryo combination therapy: an adjunctive model for the treatment of prostate cancer", Cryobiology, Jun. 2001, vol. 42, No. 4, pp. 274-285.
Corbett et al., "Biology and therapeutic response of a mouse mammary adenocarcinoma (16/C) and its potential as a model for surgical adjuvant chemotherapy", Cancer Treatment Report, Oct. 1978, vol. 62, No. 10, pp. 1471-1488.

Gage et al., "Mechanisms of tissue injury in cryosurgery", Cryobiology, Nov. 1998, vol. 37, No. 3, pp. 171-186.
Goel et al., "TNF-alpha-based accentuation in cryoinjury—dose, delivery, and response", Molecular Cancer Therapeutics, Jul. 2007, vol. 6, No. 7, pp. 2039-2047.
Han et al., "Bischof.Direct cell injury associated with eutectic crystallization during freezing", Cryobiology, Feb. 2004, vol. 48, No, 1, pp. 8-21.
Han et al., "Improved cryosurgery by use of thermophysical and inflammatory adjuvants", Technology in Cancer Research and Treatment, Apr. 2004, vol. 3, No. 2, pp. 103-111.
Ikekawa et al., "Basic studies of cryochemotherapy in a murine tumor system", Cryobiology, Oct. 1985, vol. 22, No. 5, pp. 477-483.
Kawaguchi et al., "Cryoimmunological therapy with local injection of OK-432 against advance or recurrent breast cancer", Gan To Kagku Ryoho: Cancer and Chemotherapy, Oct. 2003, vol. 30, No. 11, pp. 1583-1586.
Koushafar et al., "Effect of antifreeze proteins on frozen primary prostatic adenocarcinoma cells", Urology, May 1997, vol. 49, No. 3, pp. 421-425.
Mir et al., "Treatment of cancer with cryochemotherapy", British Journal of Cancer, May 2002, vol. 86, No. 10, pp. 1658-1660.
Mosmann, "Rapid colorimetric assay for cellular growth and survival: application to proliferation and cytotoxicity assays", Journal of Immunological Methods, Dec. 1983, vol. 65, No. 1-2, pp. 55-63.
Pham et al., "An in vivo study of antifreeze protein adjuvant cryosurgery", Cryobiology, Mar. 1999, vol. 38, No. 2, pp. 169-175.
Sabel, "Cryoablation for breast cancer: no need to turn a cold shoulder", Journal of Surgical Oncology, May 2008, vol. 97, No. 6, pp. 485-486.
Sabel et al., "Cryoablation of early-stage breast cancer: work-in-progress report of a multi-institutional trial", Annals of Surgical Oncology, May 2004, vol. 11, No. 5, pp. 542-549.
Spooimath et al., "Multifunctional Core/Shell Nanoparticles Self-Assembled from pH-Induced Thermosensitive Polymers for Targeted Intracellular Anticancer Drug Delivery", Advanced Functional Materials, Feb. 2007, vol. 17, No. 3, pp. 355-362.
Sugiyama et al., "Therapeutic effect of multimodal therapy, such as cryosurgery, locoregional immunotherapy and systematic chemotherapy against far advanced breast cancer", Gan To Kagaku Ryoho: Cancer and Chemotherapy, Oct. 2001, vol. 28, No. 11, pp. 1616-1619.
Wang et al., "An amino acidic adjuvant to augment cryoinjury of MCF-7 breast cancer cells", Cryobiology, Aug. 2008, vol. 57, No. 1, pp. 52-59.
Wong et al., "Surface Modification of Thermoresponsive Microgels via Layer-by-Layer Assembly of Polyelectrolyte Multilayers", Progress in Colloid and Polymer Science , May 2006, vol. 133, pp. 45-51.

(Continued)

*Primary Examiner* — Frederick Krass
*Assistant Examiner* — Isaac Shomer
(74) *Attorney, Agent, or Firm* — Dority & Manning, P.A.

(57) ABSTRACT

In accordance with certain embodiments of the present disclosure, a method for intracellular delivery of small molecules is provided. The method includes encapsulation of small molecules in a thermally responsive nanocapsule by decreasing the temperature of the nanocapsule to increase the permeability of the nanocapsule and allowing the small molecules to be suck into or diffuse into the nanocapsule. The nanocapsule is delivered into a cell by increasing the temperature of the nanocapsule. The small molecules are released from the nanocapsule into the cell in a controllable manner by cooling and heating treatments.

11 Claims, 17 Drawing Sheets

OTHER PUBLICATIONS

Zhang et al., "Nanoencapsulation of trehalose for intracellular delivery and controlled release using a thermally responsive polymeric nanocapsule", Biomaterials, 2009. under review.

Acker et al., "Engineering desiccation tolerance in mammalian cells: Tools and techniques", in Life in the Frozen State, Fuller et al. editors, Boca Raton, FL: CRC Press LLC, 2004. p. 563-581.

Acker et al., "Measurement of trehalose loading of mammalian cells porated with a metal-actuated switchable pore", Biotechnology and Bioengineering, Jun. 2003, vol. 82, No. 5, pp. 525-532.

Alexandris et al., "Poly(Ethylene Oxide)-Poly(Propylene Oxide)-Poly(Ethylene Oxide) Block-Copolymer Surfactants in Aqueous-Solutions and at Interfaces—Thermodynamics, Structure, Dynamics, and Modeling", Colloids and Surfaces a-Physicochemical and Engineering Aspects, Mar. 1995, vol. 96, No. 1-2, pp. 1-46.

Bae et al., "Oil-encapsulating PEO-PPO-PEO/PEG shell cross-linked nanocapsules for target-specific delivery of paclitaxel", Biomacromolecules, Feb. 2007, vol. 8, No. 2, pp. 650-656.

Bae et al., "'On-off' thermocontrol of solute transport. I. Temperature dependence of swelling of N-isopropylacrylamide networks modified with hydrophobic components in water". Pharmaceutical Research, Apr. 1991, vol. 8, No. 4, pp. 531-537.

Bae et al., "'On-off' thermocontrol of solute transport. II. Solute Release from thermosensitive hydrogels", Pharmaceutical Research, May 1991, vol. 8, No. 5, pp. 624-628.

Beattie et al., "Trehalose: a cryoprotectant that enhances recovery and preserves function of human pancreatic islets after long-term storage", Diabetes, Mar. 1997, vol. 46, No. 3, pp. 519-523.

Bhowmick et al. "Osmometric behavior of mouse oocytes in the presence of different intracellular sugars", Cryobiology, Oct. 2002, vol. 45, No. 2, pp. 183-187.

Breunig et al., "Polymers and nanoparticles: intelligent tools for intracellular targeting", European Journal of Pharmaceuticals and Biopharmaceuticals, Jan. 2008, vol. 68, No. 1, pp. 112-128.

Callahan et al., "Semitelechelic HPMA copolymers functionalized with triphenylphosphonium as drug carriers for membrane transduction and mitochondrial localization", Biomacromolecules, Aug. 2006, vol. 7, No. 8, pp. 2347-2356.

Chen et al., "Beneficial effect of intracellular trehalose on the membrane integrity of dried mammalian cells", Cryobiology, Sep. 2001, vol. 43, No. 2, pp. 168-181.

Choi et al., "Temperature-sensitive pluronic/ poly(ethylenimine) nanocapsules for thermally triggered disruption of intracellular endosomal compartment", Biomacromolecules, Jun. 2006, vol. 7, No. 6, pp. 1864-1870.

Choi et al., "Thermally reversible pluronic/heparin nanocapsules exhibiting 1000-fold volume transition", Langmuir, Feb. 2006, vol. 22, No. 4, pp. 1758-1762.

Choi et al., "Galactosylated poly(N-isopropylacrylamide) hydrogel submicrometer particles for specific cellular uptake within hepatocytes", Journal of Colloid and Interface Science, Jul. 2002, vol. 251, No. 1, pp. 57-63.

Crowe et al., "Preservation of mammalian cells—learning nature's tricks", Nature Biotechnology, Feb. 2000, vol. 18, No. 2, pp. 145-146.

Crowe et al., "Stabilization of dry mammalian cells: Lessons from nature", Integrative and Comparative Biology, Nov. 2005, vol. 45, No. 5, pp. 810-820.

Crowe et al., "Stabilization of membranes in human platelets freeze-dried with trehalose", Chemistry and Physics of Lipids, Jan. 2003, vol. 122, No. 1-2, pp. 41-52.

Crowe et al., "The role of vitrification in anhydrobiosis", Annual Review of Physiology, Mar. 1998, vol. 60, pp. 73-103.

Crowe et al., "The trehalose myth revisited: Introduction to a symposium on stabilization of cells in the dry state", Cryobiology, Sep. 2001, vol. 43, No. 2, pp. 89-105.

Croy et al., "Polymeric micelles for drug delivery", Current Pharmaceutical Design, 2006, vol. 12, No. 36, pp. 4669-4684.

Dunn et al., "Long-term in vitro function of adult hepatocytes in a collagen sandwich configuration", Biotechnology Progress, May-Jun. 1991, vol. 7, No. 3, pp. 237-245.

Elliott et al., "Trehalose uptake through P2X7 purinergic channels provides dehydration protection", Cryobiology, Feb. 2006, vol. 52, No. 1, pp. 114-127.

Eroglu et al., "Beneficial effect of microinjected trehalose on the cyrosurvival of hyman oocytes", Fertility Sterility, Jan. 2002, vol. 77, No. 1, pp. 152-158.

Eroglu et al., "Intracellular trehalose improves the survival of cryopreserved mammalian cells", Nature Biotechnology, Feb. 2000, vol. 18, No. 2, pp. 163-167.

Eroglu et al., "Progressive elimination of microinjected trehalose during mouse embryonic development", Reproductive BioMedicine Online, Apr. 2005, vol. 10, No. 4, pp. 503-510.

Eroglu et al., "Quantitative microinjection of trehalose into mouse oocytes and zygotes, and its effect on development", Cryobiology, Apr. 2003, vol. 46, No. 2, pp. 121-134.

Gao et al., "Thermosensitive poly (allylamine)-g-poly (N-isopropylacrylamide): synthesis, phase separation and particle formation", Polymer, May 2005, vol. 46, No. 12, pp. 4088-4097.

Gao et al., "Thermosensitive poly (N-isopropylacrylamide) nanocapsules with controlled permeability", Polymer, Feb. 2005, vol. 46, No, 4, pp. 1087-1093.

Gearhart, "New potential for human embryonic stem cells", Science, Nov. 1998, vol. 282, No. 5391, pp. 1061-1062.

Gordon et al., "Recovery of human mesenchymal stem cells following dehydration and rehydration", Cryobiology, Sep. 2001, vol. 43, No. 2, pp. 182-187.

Griffiths et al., "A quantitative analysis of the endocytic pathway in a baby hamster kidney cells", Journal of Cell Biology, Dec. 1989, vol. 109, No. 6 Pt 1, pp. 2703-2720.

Guo et al., "Trehalose expression confers desiccation tolerance on human cells", Nature Biotechnology, Feb. 2000, vol. 18, No. 2, pp. 168-171.

Haussinger, "The role of cellular hydration in the regulation of cell function", Biochemical Journal, Feb. 1996, vol. 313, pp. 697-710.

He et al., "Water activity and mobility in solutions of glycerol and small molecular weight sugars: Implication for cryo- and lyopreservation", Journal of Applied Physics, Oct. 2006, vol. 100, No. 7, pp. 0747021-07470211.

He et al., "Thermally induced introduction of trehalose into primary rat hepatocytes", Cell Preservation Technology, Nov. 2006; 4(3):178-187.

Holovati et al., "Spectrophotometric measurement of intraliposomal trehalose", Cryobiology, Oct. 2007, vol. 55, No. 2, pp. 98-107.

Isaacks et al., "Effect of osmolality and anion channel inhibitors on myo-inositol efflux in cultured astrocytes", Journal of Neuroscience Research, Sep. 1999, vol. 57, No. 6, pp. 866-871.

Jeong et al., "Drug release from biodegradable injectable thermosensitive hydrogel of PEG-PLGA-PEG triblock copolymers", Journal of Controlled Release, Jan. 2000, vol. 63, No. 1-2, pp. 155-163.

Jeong et al., "Thermosensitive sol-gel reversible hydrogels", Advanced Drug Delivery Reviews, Jan. 2002, vol. 54, No. 1, pp. 37-51.

Kabanov et al., "Pluronic block copolymers as novel polymer therapeutics for drug and gene delivery", Journal of Controlled Release, Aug. 2002, vol. 82, No. 2-3, pp. 189-212.

Kirk, "Swelling-activated organic osmolyte channels", Journal of Membrane Biology, Jul. 1997, vol. 158, No. 1, pp. 1-16.

Kitowska et al., "Functional role and species-specific contribution of arginases in pulmonary fibrosis", American Journal of Physiology—Lung Cellular and Molecular Physiology, Jan. 2008, vol. 294, No. 1, pp. L34-L45.

Langer et al., "Tissue Engineering", Science May 1993, vol. 260, No. 5110, pp. 920-926.

Lee et al., "Thermally sensitive cationic polymer nanocapsules for specific cytosolic delivery and efficient gene silencing of siRNA: swelling induced physical disruption of endosome by cold shock", Journal of Controlled Release, Jan. 2008, vol. 125, No. 1, pp. 25-32.

Lee et al., "Regional delivery of vancomycin using pluronic F-127 to inhibit methicillin resistant *Staphylococcus aureus* (MRSA) growth in chronic otitis media in vitro and in vivo", Journal of Controlled Release, Apr. 2004, vol. 96, No. 1, pp. 1-7.

Liu et al., "Trehalose loading through the mitochondrial permeability transition pore enhances desiccation tolerance in rat liver mitochondria", Biochimica et Biophysica Acta, Nov. 2005, vol. 1717, No. 1, pp. 21-26.

Liu et al., "Thermally responsive piolymeric micellar nanoparticles self-assembled from cholesteryl end-capped random poly(N-isopropylacrylamide-co-N,N-dimethylacrylamide): synthesis, temperature-sensitivity, and morphologies", Journal of Colloid and Interface Sciences, Oct. 2005, vol. 266, No. 2, pp. 295-303.

Lloyd, "Lysosome membrane permeability: implications for drug delivery", Advanced Drug Delivery Reviews, Mar. 2000, vol. 41, No. 2, pp. 189-200.

Malmsten et al., "Self-Assembly in Aqueous Block Copolymer Solutions", Macromolecules, Sep. 1992, vol. 25, No. 20, pp. 5440-5445.

Maxfield et al., "Endocytic recycling", Nature Reviews of Molecular Cell Biology, Feb. 2004, vol. 5, No. 2, pp. 121-132.

McGraw, "Internalization and sorting of macromolecules: endocytosis" In: Juliano RL, editor. Targeted Drug Delivery. New York: Springer-Verlag, 1991.

Nguyen et al., "Amphiphilic linear-dendritic triblock copolymers composed of poly(amidoamine) and poly(propylene oxide) and their micellar-phase and encapsulation properties", Langmuir, Aug. 2006, vol. 22, No. 18, pp. 7825-7832.

Nimesh et al., "Polyethylenimine nanoparticles as efficient transfecting agents for mammalian cells", Journal of Controlled Release, Jan. 2006, vol. 110, No. 2, pp. 457-468.

Oh et al., "Micellar formulations for drug dlivery based on mixtures of hydrophobic and hydrophilic Pluronic block copolymers", Journal of Controlled Release, Feb. 2004, vol. 94, No. 2-3, pp. 411-422.

Oh et al., "Formation of core/shell nanoparticles with a lipid core and their application as a drug delivery system", Biomacromolecules, Mar.-Apr. 2005, vol. 6, No. 2, pp. 1062-1067.

Oh et al., "Core/Shell nanoparticles with lecithin lipid cores for protein delivery", Biomacromolecules, Aug. 2006, vol. 7, No. 8, pp. 2362-2367.

Oliver et al., "Loading MSCs with trehalose by endocytosis", Cell Preservation Technology, Jul. 2004, vol. 2, No. 1, pp. 35-49.

Patton et al., "Engineering temperature-sensitive hydrogel nanoparticles entrapping hemoglobin as a novel type of oxygen carrier", Biomacromolecules, Jul.-Aug. 2005, vol. 6, No. 4, pp. 2204-2212.

Pedersen et al., "Possible interrelationship between changes in F0-actin and myosin II, protein phosphorylation, and cell volume regulation in Ehrlich ascites tumor cells", Experimental Cell Research, Jul. 2002, vol. 277, No. 1, pp. 57-73.

Puhlev et al., "Desiccation tolerance in human cells", Cryobiology, May 2001; vol. 42, No. 3, pp. 207-217.

Ramkissoon-Ganorkar et al., "Polymer molecular weight alters properties of pH-/temperature-sensitive polymeric beads", Pharmaceutical Research, Jun. 1999, vol. 16, No. 6, pp. 819-827.

Ramkissoon-Ganorkar et al., "Effect of molecular weight and polydispersity on kinetics of dissolution and release from pH-/temperature-sensitive polymers", Journal of Biomaterials Science, Polymer Edition, Jun. 1999, vol. 10, No. 10, pp. 1149-116.

Rejman et al., "Size-dependent internalization of particles via the pathways of clathrin- and caveolae-mediated endocytosis", Biochemical Journal, Jan. 2004, vol. 366, Pt.1, pp. 159-169.

Reuss et al., "Intracellular delivery of carbohydrates into mammalian cells through swelling-activated pathways", Journal of Membrane Biology, Jul. 2004, vol. 200, No. 2, pp. 67-81.

Ricker et al., "Trehalose maintains phase separation in an air-dried binary lipid mixture", Biophysical Journal, May 2003, vol. 84, No. 5, pp. 3045-3051.

Robinson et al., "Preparation and characterization of pH-responsive poly(methacrylic acid-g-ethylene glycol) nanospheres", Macromolecules, Apr. 2002, vol. 35, No. 9, pp. 3668-3674.

Satpathy et al., "Loading red blood cells with trehalose: a step towards biostabilization", Cryobiology, Oct. 2004, vol. 49, No. 2, pp. 123-136.

Schild, "Poly (N-Isopropylacrylamide)—Experiment, Theory, and Application", Progress in Polymer Science, 1992, vol. 17, No. 2, pp. 163-249.

Scott et al., "Response of hemotopoietic progenitor cells to trehalose-loaded liposomes", Cryobiology, 2006, vol. 53, pp. 380.

Serres et al., "Temperature and pH-sensitive polymers for human calcitonin delivery", Pharmaceutical Research, Feb. 1996, vol. 13, No. 2, pp. 196-201.

Sershen et al., "Temperature-sensitive polymer-nanoshell composites for photothermally modulated drug delivery", Journal of Biomedical Materials Research, Sep. 2000, vol. 51, No. 3, pp. 293-298.

Shirakashi et al., "Intracellular delivery of trehalose into mammalian cells by electropermeabilization", Journal of Membrane Biology, Sep. 2002, vol. 189, No. 1, pp. 45-54.

Tirelli, "(Bio)Responsive nanoparticles", Current Opinion in Colloid & Interface Science, Oct. 2006, vol. 11, No. 4, pp. 210-216.

Toner et al., "Storage and Translational issues in reparative medicine", Annals of the NY Academy of Sciences, Jun. 2002, vol. 961, pp. 258-262.

Vasir et al., "Biodegradable nanoparticles for cytosolic delivery of therapeutics", Advanced Drug Delivery Reviews, Aug. 2007, vol. 59, No. 8, pp. 718-728.

Vinogradov et al., "Nanosized cationic hydrogels for drug delivery: preparation, properties, and interactions with cells", Advanced Drug Delivery Reviews, Jan. 2002, vol. 54, No. 1, pp. 135-147.

Vinogradov et al., "Nanogels for oligonucleotide delivery to the brain", Bioconjugate Chemistry, Jan.-Feb. 2004, vol. 15, No. 1, pp. 50-60.

Wittemann et al., "Biocompatible polymer vesicles from biamphiphilic triblock copolymers and their interaction with bovine serum albumin", Langmuir, Feb. 2007, vol. 23, No. 4, pp. 2224-2230.

Wolkers et al., "From anhydrobiosis to freeze-drying of eukaryotic cells", Comparative Biochemistry and Physiology, Part A: Molecular and Integrative Physiology, Mar. 2002, vol. 131, No. 3, pp. 535-543.

Wolkers et al., "Human platelets loaded with trehalose survive freeze-drying", Cryobiology, Mar. 2001, vol. 42, No. 2, pp. 79-87.

Wolkers et al., "Temperature dependence of fluid phase endocytosis coincides with membrane properties of pig platelets", Biochimica et Biophysica Acta, Jun. 2003, vol. 1612, No. 2, pp. 154-163.

Wood et al., "Tumor-targeted gene delivery using molecularly engineered hybrid polymers functionalized with a tumor-homing peptide", Bioconjugate Chemistry, Feb. 2008, vol. 19, No. 2, pp. 403-405.

Wood et al., "Tunable drug release from hydrolytically degradable layer-by-layer thin films", Langmuir, Feb. 2005, vol. 21, No. 4, pp. 1603-1609.

Xiong et al., "Synthesis and thermally responsive properties of novel pluronic F817/polycaprolactone (PCL) block copolymers with short PCL blocks", Journal of Applied Polymer Science, Jun. 2006, vol. 100, No. 5, pp. 4163-4172.

* cited by examiner

A  B

Cold shock

Without cold shock

Blue fluorescence: Nucleus stain (hoechst); Green fluorescence: FITC-labeled nanocapsules; Red fluorescence: lysosome/endosome A: DIC image B: Nucleus stain (Hoechst)

C: EB

D: Merged image of B and C

E: Merged image of A, B and C

A: DIC image

B: Nucleus stain (Hoechst)

C: EB

D: Merged image of B and C

E: Merged image of A, B and C

A: DIC image

B: Nucleus stain (Hoechst)

C: EB

D: Merged image of B and C

E: Merged image of A, B and C after Removal of free EB, confocal images

A: DIC image

B: Nucleus stain (Hoechst)

C: EB

D: Merged image of B and C

E: Merged image of A, B and C

Left panel: phase contrast image

Right panel: Green fluorescence (GFP)

US 8,318,207 B2

ENCAPSULATION AND CONTROLLED RELEASE OF SMALL MOLECULES FOR INTRACELLULAR DELIVERY USING THERMALLY RESPONSIVE NANOCAPSULES

CROSS-REFERENCE TO RELATED APPLICATION

The present application is based on and claims priority to U.S. Provisional Application 61/207,485 having a filing date of Feb. 12, 2009, which is incorporated by reference herein.

BACKGROUND OF THE INVENTION

Trehalose, a non-reducing disaccharide of glucose, is found at high concentrations in organisms that are capable of withstanding extreme drought and/or cold conditions in nature (i.e., anhydrobiosis or life without water). Moreover, trehalose has been demonstrated to be a potent, nontoxic bioprotectant for stabilizing lipids, proteins, viruses, blood cells and even eukaryotic mammalian cells (e.g., oocytes) at cryogenic and particularly, ambient temperatures (i.e., cryo and lyopreservation). Unfortunately, mammalian cells lack a mechanism to synthesize trehalose and the sugar cannot permeate their plasma membrane. However, trehalose must present both intra and extracellularly to protect cells from being damaged by the dehydration and/or freezing stresses during cryo and lyopreservation. Therefore, it is crucial to develop an effective approach that can deliver trehalose into mammalian cells as the first step toward long-term biostabilization of mammalian cells using the sugar, particularly at an ambient temperature. Due to the limited availability of cell sources, long-term cell biostabilization for future use is critical to the success of the emerging cell-based medical technologies such as tissue engineering, regenerative medicine, cell/organ transplantation, stem cell therapy, and assisted reproduction.

A number of methods have been explored to introduce trehalose within mammalian cells over the past two decades. The most straightforward approach is to deliver exogenous trehalose into the cytoplasm by direct microinjection. This approach has been successfully applied to oocytes that have a large size (~100 μm in diameter) and are generally in a small quantity (tens or at most hundreds). However, it has difficulty to be applied to most mammalian cells that are generally much smaller (<20 μm) and in large quantities (usually millions). Mammalian cells have been genetically engineered to synthesize trehalose for biostabilization. This approach requires the constant production of adenoviral vectors at high multiplicities of infection that was found to exhibit significant cytotoxicity. Trehalose has also been introduced within mammalian cells or their organelles through engineered or natured transmembrane pores, electroporation, fluid-phase endocytosis, and lipid phase transition. More recently, liposomes have being investigated to encapsulate trehalose as a potential intracellular delivery vehicle of the sugar. However, consistent report of cryo and lyopreservation using trehalose delivered intracellularly via the above-mentioned approaches for small (<20 μm) eukaryotic mammalian cells, is still absent. This could be due to the inability to deliver a sufficient amount of intracellular trehalose (i.e., 0.1 M or more) for cellular protection using some of the approaches (e.g., fluid phase endocytosis). In addition, cells could be too severely compromised during the trehalose delivery steps to withstand further cryo/dehydration stress, considering the highly invasive nature of some of the approaches (e.g., electroporation).

Therefore, further investigation to develop a minimally invasive approach capable of delivering sufficient intracellular trehalose or similar agents for biostabilization is in need. Further, there is a more general need for efficient mechanisms for encapsulation and controlled release of small molecules for intracellular delivery.

SUMMARY

In accordance with certain embodiments of the present disclosure, a method for intracellular delivery of small molecules is provided. The method includes encapsulation of small molecules in a thermally responsive nanocapsule by decreasing the temperature of the nanocapsule to increase the permeability of the nanocapsule and allowing the small molecules to be sucked into or diffuse into the nanocapsule. The nanocapsule is delivered into a cell by increasing the temperature of the nanocapsule. The small molecules are released from the nanocapsule into the cell.

In accordance with still other aspects of the present disclosure, a thermally responsive nanocapsule comprising is provided. The nanocapsule comprises a polymeric hydrogel nanocapsule which includes a shell and a core. The shell has a diameter of greater than 150 nm at a temperature of less than 25° C. and a diameter of less than 150 nm at a temperature of greater than 25° C.

BRIEF DESCRIPTION OF THE FIGURES

A full and enabling disclosure of the present subject matter, including the best mode thereof, to one of ordinary skill in the art, is set forth more particularly in the remainder of the specification, including reference to the accompanying figures in which.

DETAILED DESCRIPTION OF REPRESENTATIVE EMBODIMENTS

Figure 1:
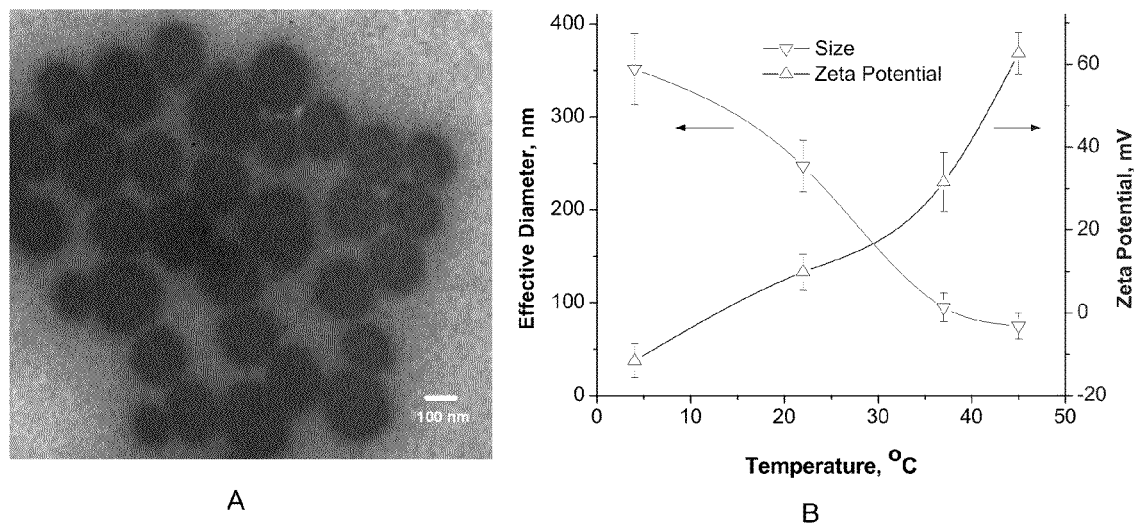
FIG. 1. Morphology and thermal responsiveness of the synthesized Pluronic F127-PEI (polyethylenimine) nanocapsules demonstrated by a typical TEM (transmission electron microscopy) image of the nanocapsules (A) and the effective diameter and surface zeta potential measured by DLS (dynamic light scattering, B), respectively. Error bar represents standard deviation. Scale bar: 100 nm FIG. 2. A schematic representation of the Pluronic F127-PEI nanocapsules at 22 and 37° C.: PPO, polypropylene oxide; PEO, polyethylene oxide; and PEI, polyethylenimine. The plus symbol represents positive charge.

Reference will now be made in detail to embodiments of the disclosed subject matter, one or more examples of which are set forth below. Each example is provided by way of explanation of the subject matter, not limitation of the subject matter. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

In general, the present disclosure is directed to encapsulation and controlled release of small molecules for intracellular delivery using thermally responsive nanoparticles.

Polymeric nanoparticles are a useful tool to encapsulate therapeutic drugs, genes, and proteins for their controlled and sustained delivery. Among them, polymeric hydrogel nanoparticles with thermal and/or pH responsiveness are particularly attractive as vehicles for delivery and release of small molecules. Many polymeric hydrogel nanoparticles exhibit a lower critical solution temperature (LOST), which can be designed to be between about 20-35° C. The polymeric hydrogel is in a swollen/soluble state at or below room temperature, while it is in a collapsed/gel state at the physiological temperature (i.e., about 37° C.). The sol-gel transition of the hydrogel is accompanied with an apparent change of its chemical and physical properties, which could be utilized to achieve controlled release of drug and therapeutic agents encapsulated in the hydrogel. For example, hydrophilic and hydrophobic therapeutic agents can be effectively encapsulated in appropriately designed Pluronic hydrogel nanocapsules with minimum release (less than about 20%) for up to 2 days at a temperature above the hydrogel LOST. Nanocapsules less than about 150 nm can be easily internalized by mammalian cells via endocytosis, a natural pathway of cell self-feeding. Furthermore, the surface of the nanocapsules can be modified using ligands and/or other functional moieties such as polyethylenimine (PEI) to achieve target specific and/or facilitated intracellular delivery of therapeutic agents.

In accordance with the present disclosure, a thermally responsive polymeric hydrogel nanocapsule was synthesized, characterized, and used as the vehicle for delivering various therapeutic drugs, genes, and proteins. The nanocapsule was made of Pluronic F127 and polyethylenimine (PEI), although any suitable materials could be utilized in accordance with the present disclosure. For instance, a triblock polymer poly(ethylene oxide)-polypropylene oxide)-poly(ethylene oxide), which is commercially available under the PLURONIC™ or POLOXAMER™ trade names, can be utilized to form the nanocapsule of the present disclosure. In addition, the nanocapsule can include polyethylenimine, chitosan, poly-l-lysine, or other polycations can be utilized to form the nanocapsule of the present disclosure. In certain embodiments, the nanocapsule can be formed using poly(N-isopropylacrylamide) or another amphiphilic polymer that exhibits a LOST of from about 4° C. to about 37° C.

The nanocapsule can be loaded with therapeutic drugs, genes, and proteins, or the like such as exogenous trehalose. The nanocapsule can be delivered to any suitable type of cell including mammalian cells. The temperature dependent properties (i.e., thermal responsiveness) of the nanocapsule such as size, surface charge, and particularly wall permeability were utilized to achieve nanoencapsulation and controlled release of therapeutic drugs, genes, and proteins both outside and inside mammalian cells (i.e., NIH 3T3 fibroblasts here). In certain embodiments, trehalose can be utilized in nanocapsules of the present disclosure. In certain embodiments, the nanoparticles can be loaded with DNA plasmids, siRNA, microRNA, or combinations thereof.

For instance, in one particular embodiment, it was found that a significant amount of trehalose that is sufficient for biostabilization can be delivered into the cells using the Pluronic F127-PEI nanocapsule. It was further found that cytotoxicity of the nanocapsules is negligible for the purpose of trehalose delivery.

The nanocapsules of the present disclosure can be surface-modified using polyethylene glycol or other stealth materials for in vivo drug delivery. In addition, the nanocapsules can be surface-modified using folic acid or other targeting moieties for target specific in vivo drug delivery. However, such examples are not meant to be limiting and any suitable compounds can be used to surface-modify the nanocapsules of the present disclosure.

Reference now will be made to exemplary embodiments of the invention set forth below. Each example is provided by way of explanation of the invention, not as a limitation of the invention.

EXAMPLE 1

In the present study, a thermally responsive polymeric hydrogel nanocapsule made of Pluronic F127 and polyethylenimine (PEI) was synthesized, characterized, and used as the vehicle for delivering exogenous trehalose into mammalian cells. The temperature dependent properties (i.e., thermal responsiveness) of the nanocapsule such as size, surface charge, and particularly wall permeability were utilized to achieve nanoencapsulation and controlled release of trehalose both outside and inside mammalian cells (i.e., NIH 3T3 fibroblasts here). It was found that a significant amount of trehalose that is sufficient for biostabilization can be delivered into the cells using the Pluronic F127-PEI nanocapsule. It was further found that cytotoxicity of the nanocapsules is negligible for the purpose of trehalose delivery.

2. Materials and Methods 2.1. Materials

Pluronic F127 (12.6 kDa) manufactured by BASF Corp. (Wyandotte, Mich.) was used. LysoTracker Red DND-99, and Viability/Cytotoxicity kit for mammalian cells were purchased from Invitrogen (Carlsbad, Calif.). The dihydrate of α,α-trehalose (high purity) was purchased from Ferro Pfanstiehl Laboratories (Waukegan, Ill.). Polyethylenimine (PEI, MW=2 kDa), 4-nitrophenyl chloroformate, and fluorescein isothiocyanate (FITC) were purchased from Sigma (St Louis, Mo.) and used as received.

2.2. Synthesis of Pluronic F127-PEI Nanocapsules

The thermally responsive Pluronic F127-PEI nanocapsule was prepared using a modified emulsification/solvent evaporation method with slight modification. Briefly, Pluronic F127 was pre-activated at both terminals with 4-nitrophenyl chloroformate that contains an amine-specific reactive group. The activated Pluronic F127 was then dissolved in dichloromethane (i.e., oil) at a concentration of 20% (w/v) and added drop-wise into an aqueous solution of 0.75% (w/v) PEI with a pH of 9. The oil-in-water mixture was emulsified for 4 min using a Branson 450 Sonifier (Danbury, Conn.). Pluronic F127-PEI nanocapsules were formed as a result of the interfacial crosslinking reaction between the pre-activated Pluronic F-127 in oil and PEI in water at the oil-in-water interface. Organic solvents (i.e., dichloromethane) in the emulsion were then removed by evaporation using a rotary evaporator until the solution became clear. The sample was then dialyzed against water at pH 4.0 with a Spectra/Por (Spectrum Labs, Rancho Dominguez, Calif.) dialysis tube (MWCO, 50 kDa) to remove non-crosslinked Pluronic F127 and PEI and any residual organic solvents. Water in the sample was then removed by freeze drying and the resultant dry nanocapsules were either used immediately or kept at $-20°$ C. for future use.

2.3. Characterization of Nanocapsule Morphology, Size, and Surface Charge

The morphology of the synthesized nanocapsules was studied using transmission electron microscopy (TEM). For TEM analysis, one drop (2 μl) of the aqueous nanocapsule solution (2 mg/ml) was dried on a copper TEM grid for at least 10 min. The dried nanocapsule specimen was then stained by adding a drop (~2 μl) of 2% (w/v) uranyl acetate solution followed by drying for at least 10 min. The sample was then examined using a Hitachi H-800 transmission electron microscope. All the procedures were performed at room temperature. The size and surface charge (represented by the surface ζ potential) of the synthesized nanocapsule at various temperatures from 4-45° C. was further measured using a Brookhaven (Holtsville, N.Y.) ZetaPlus dynamic light scattering (DLS) instrument, for which the nanocapsule was dissolved in 1x phosphate-buffered saline (PBS) at a concentration of 1 mg/ml.

2.4. Cell Culture

NIH 3T3 fibroblasts were cultured in high glucose DMEM (Invitrogen, Carlsbad, Calif.) supplemented with 10% fetal bovine serum (Hyclone, Logan, Utah), 100 U/ml penicillin and 100 μg/ml streptomycin (Hyclone, Logan, Utah) at 37° C. in a humidified 5% $CO_2$ incubator.

2.5. Cellular Uptake and Intracellular Distribution of the Nanocapsule

To study cellular uptake and the subsequent intracellular distribution of the Pluronic F127-PEI nanocapsules, they were first labeled with the fluorescent probe FITC. A total of 60 mg of the freeze-dried nanocapsules was dissolved in 4.6 ml of 0.1 M sodium carbonate buffer at pH 9, followed by adding dropwise a total of 220 μl of 26 mM FITC solution (in DMSO). FITC labeling of the nanocapsules was done by allowing the solutions to react for 8 h at 4° C. under gentle and continuous shaking in the dark. A total of 2.2 mg ammonium chloride was then added into the solution for 2 h at 4° C. to quench the reaction. The FITC labeled nanocapsules were further purified by dialysis against deionized water in the dark for 24 hours with the water being replaced every 3-5 hours.

To study cellular uptake of the FITC labeled nanocapsules, NIH 3T3 cells were seeded in 33 mm Petri dishes at a density of $5 \times 10^5$ cells/dish in 1 ml medium. After 24 h, the culture medium was replaced with serum-free medium containing FITC-labeled nanocapsules (100 μg/ml) and LysoTracker Red DND-99 (55 nM). The latter is a fluorescent probe that can permeate cell plasma membrane and accumulates in subcellular organelles with an acidic internal environment such as the endosome and lysosome. After incubation for 40 min at 37° C., cells were washed three times using warm 1x phosphate-buffered saline (PBS). The cells were then fixed using 4% warm paraformaldehyde for 20 min either immediately or after a cold shock treatment by incubating the cells in 1x PBS for 15 min at 22° C. After fixation, the cells were washed using 1x PBS and intracellular distribution of FITC-labeled nanocapsules in the cells was examined using a confocal microscope (LSM 510, Carl-Zeiss Inc, Oberkochen, Germany) with fluorescent capability.

2.6. Cytotoxicity of the Synthesized Nanocapsules

Both immediate cell viability and long-term cell proliferation were studied to test the cytotoxicity of the nanocapsules synthesized. For immediate cell viability study (i.e., short-term toxicity), NIH 3T3 cells were seeded in 33 mm Petri dishes at a density of $5 \times 10^5$ cells/dish in 1 ml medium. After 24 h, the cell culture medium was replaced with warm (37° C.) serum-free medium containing nanocapsules of various concentrations. After incubating for 40 min at 37° C., cells were washed three times using warm (37° C.) 1x PBS to remove any extracellular nanocapsules followed by a cold shock treatment in fresh culture medium for 15 min at 22° C. Cell viability of the cells immediately after cold shock was determined using the standard live/dead assay kit purchased from Invitrogen. The cell membrane permeable calcein AM (5 μM) in the kit could be converted to the intensely green fluorescent calcein which can be well retained within live cells with intact plasma membrane. Ethidium homodimer (EthD-1, 5 μM), the other fluorescent probe in the kit, enters cells with a compromised plasma membrane (taken as dead cells) and binds to nucleic acids producing bright red fluorescence while it is excluded by the intact plasma membrane of viable cells. The cells were examined using an Olympus BX 51 microscope equipped with fluorescent cubes and a QICAM CCD digital camera (Qlmaging, Surrey, BC, Canada). At least 10 representative images were taken and processed using the Linksys 32 software (Linkam, UK) to count viable (green fluorescence) and dead (red fluorescence) cells. Immediate cell viability was calculated as the ratio of the number of viable cells to the total number of cells, which were at least 1200 for each sample.

For long-term cell proliferation studies, cells were seeded in 33 mm Petri dishes at a relatively low density of $1 \times 10^5$ cells/dish in 1 ml medium. At 24 h, the cells were exposed to nanocapsules in the same way as that described above for immediate cell viability studies. After cold shock, the cells were further cultured for 3 days to monitor their proliferation (long-term toxicity). This was done by taking at least 10 representative images of the samples every day including the day (taken as day 0) when the cells were exposed to nanocapsules. The total number of cells in each image were counted automatically using NIH ImageJ.

2.7. Nanoencapsulation and Controlled Release of Trehalose

Nanoencapsulation of trehalose was done in two steps: 1), incubating the nanocapsules (10 mg/ml) with trehalose (15% w/v) in water overnight (~12 hr) at room temperature (~22° C.) when the nanocapsules were swollen and their wall permeability was high and 2) freeze-drying the sample to remove water both inside and outside the nanocapsules. Trehalose diffused into the nanocapsule during the incubating step should remain in the nanocapsule after freeze drying. The resultant freeze-dried mixture of extra-capsular trehalose and trehalose-loaded nanocapsules was either used immediately or stored at −20° C. for future use.

To determine whether trehalose can be withheld in the nanocapsule at 37° C. for controlled release, the freeze-dried mixture of trehalose and trehalose-loaded nanocapsules was preheated to 37° C. and dissolved in 2 ml warm water at 37° C. in a 15 ml centrifuge tube. The final overall trehalose (i.e., trehalose both inside and outside the nanocapsules) concentration in the solution was 15% (w/v) and the corresponding nanocapsule (excluding the encapsulated trehalose) concentration was 10 mg/ml. Therefore, the total amount of trehalose and nanocapsules (excluding the encapsulated trehalose) in the 2 ml solution was 0.3 and 0.02 g, respectively. The solution in the centrifuge tube was then transferred either after cooling at 22° C. (i.e., cold shocking) for 15 min or immediately into a Spectra/Por dialysis bag (MWCO, 50 kDa) and placed in a beaker containing 1 L of deionized water kept warm at 37° C. with constant stirring using a hotplate/stirrer for 5 hr. It is expected that the 15 min cooling at 22° C. followed by heating at 37° C. in the beaker should result in a quick release of nanoencapsulated trehalose as a result of the more than 15 times of volume expansion and contraction in response to the temperature variation. Control experiments were performed similarly except that 2 ml of 15% (w/v) pure trehalose solution (i.e., in the absence of nanocapsules) was used in the dialysis tube. At various times (i.e., 0.5, 1, 2, 3, and 5 hr), a total of 0.5 ml of the solution outside the dialysis tube in the beaker was collected to determine the trehalose concentration in the 1 L deionized water for each sample. The total liquid volume outside the dialysis tube in the beaker was kept at 1 L by adding the same amount of deionized water at each sampling time. Trehalose concentration in the 0.5 ml samples was determined using a trehalose assay kit (Megazyme Co., Wicklow, Ireland) by following the manufacturer's instructions. Briefly, trehalose in a sample was hydrolyzed to D-glucose using trehalase and the D-glucose was phosphorylated using hexokinase (HK) and adenosine-5'-triphosphae (ATP) to glucose-6-phosphate (G-6-P). In the presence of the glucose-6-phosphate dehydrogenase (G6P-DH), the produced G-6-P was oxidized by nicotinamide-adenine dinucleotide phosphate (NADP+) to gluconate-6-phosphate with the formation of reduced nicotinamide-adenine dinucleotide phosphate (NADPH). The absorbance at 340 nm of NADPH was then measured using a Shimazu (Columbia, Md.) UV-2101PC spectrophotometer to determine the amount of trehalose in the original sample.

2.8. Nanocapsule Assisted Intracellular Delivery of Trehalose

For intracellular delivery of trehalose, the freeze-dried mixture of trehalose and trehalose-loaded nanocapsules were preheated to 37° C. and dissolved in warm (37° C.) serum-free culture medium at various trehalose (or correspondingly, nanocapsule) concentrations to incubate with the 3T3 fibroblasts for uptake. The procedures performed for cellular uptake of the trehalose loaded nanocapsules was the same as that described in section 2.6 for the uptake of empty nanocapsules. After cold shock at 22° C. for 15 min, the incubating solution was decanted and the cells were further washed three times using 1x PBS. The cells were then detached/lysed in deionized water with the aid of a cell scraper. The cells were further lysed using three cycles of freezing and thawing in liquid nitrogen and 37° C. water bath, respectively. The lysed cell suspension was homogenized for 10 min by sonication using a Branson ultrasonic cleaner (Danbury, Conn.) followed by a brief vortex-mixing. After centrifuging at 10,000 g for 10 min, the supernatant of each sample was divided into two aliquots. One aliquot was used to determine trehalose concentration in the sample using the trehalose assay kit (Megazyme Co. Wicklow, Ireland) as described in the previous section. Interfering reducing sugars mainly from the cellular cytoplasm in all samples were removed using alkaline borohydride (10 mg/mL sodium borohydride in 50 mM sodium hydroxide) and excessive alkaline borohydride was neutralized using 200 mM acetic acid. The other aliquot was used to determine cell density in the sample based on its DNA content measured using a method described in Dunn et. al, Long-term in vitro function of adult hepatocytes in a collagen sandwich configuration, Biotechnol Prog 1991 May-Jun;7 (3):237-245. The osmotically active volume of a single NIH 3T3 fibroblast was reported to be $1.45 \times 10\text{-}15$ m$^3$. With the trehalose concentration and cell density in the sample being measured, the total amount of intracellular trehalose and the total number of cells (and thus the total osmotically active cell volume) can be calculated. Therefore, the intracellular trehalose concentration can be determined.

2.9. Immediate Viability, Proliferation, and Collagen Production of Trehalose Loaded Cells The immediate cell viability, proliferation, and collagen production of 3T3 cells exposed to 0.22 M extracellular trehalose and 0.5 mg/ml nanocapsules (loaded with trehalose) (As will be shown later in Results and Discussion that the intracellular trehalose is ~0.3 M under this loading condition) were further studied to test the effectiveness of the nanocapsule based approach for intracellular delivery of trehalose. Immediate cell viability and proliferation of the 3T3 cells after loading with trehalose were studied in the same way as that described for 3T3 cells loaded with empty nanocapsules in section 2.6. The collagen production of cells exposed to 0 M trehalose and 0 mg/ml nanocapsules (control), 0.22 M extracellular trehalose and 0 mg/ml nanocapsules (trehalose without NE), and 0.22 M extracellular trehalose and 0.5 mg/ml extracellular nanocapsules (nanoencapsulated with trehalose) was quantified using the Sircol™ Assay kit (Biocolor, Belfast, N. Ireland). To do this, the cells treated under the three conditions were further cultured for 3 days. The culture medium (1 ml) was collected and the cells replenished with the same amount of fresh medium every day. To measure collagen concentration in the collected medium using the Sircol assay, 20 μl of the collected medium was diluted into 50 μl using deionized water in a 1 ml centrifuge tube. Blank samples were prepared using 20 μl fresh medium and 30 μl deionized water and collagen standard samples were prepared using 20 μl fresh medium and 30 μl deionized water containing 5, 10, 15 and 20 μg collagen. A total of 0.5 ml Sircol dye reagent was then added into each sample and mixed with the sample for 30 minutes to allow binding between the dye and collagen monomers. After centrifuging for 10 min at 12,000 g, the supernatant with unbound dye in the tube was removed. The collagen bound dye was then released by adding 0.5 ml of alkali reagent included in the assay kit. The absorbance at 540 nm wavelength of the dye was then measured using a BioTek Synergy 2 microplate reader (Winooski, Vt.). Collagen concentration in the collected medium was quantified by comparing its absorbance subtracted with the absorbance of the blank sample with that of the standards.

2.10. Statistical Analysis

All results were reported as the mean and standard deviation of data from at least three replicates. Student's two-tailed t-test assuming equal variance was calculated using Microsoft® Excel to determine statistical significance ($p<0.05$).

3. Results and Discussion 3.1. Nanocapsule Morphology, Size, and Surface Charge

A typical TEM image of the synthesized Pluronic F127-PEI nanocapsules is shown in FIG. 1A. The nanocapsule is round in shape and its size distribution is quite uniform. The size of the nanocapsule was further measured by dynamic light scattering (DLS) at various temperatures from 4 to 45° C. and the results are shown in FIG. 1B. Clearly, a broad thermal responsiveness of the Pluronic F127-PEI nanocapsule over the temperature range is observable: it is less than 100 nm at 37° C. or higher (e.g., 95.1±15.4 nm at 37° C. and 74.9±14.0 nm at 45° C.) whereas it is more than ~250 nm at 22° C. or lower (e.g., 247.2±27.8 at 22° C. and 351.8±38.2 nm at 4° C.). Also shown in FIG. 1B is the temperature dependent surface charge of the nanocapsule represented by the surface zeta ($\zeta$) potential. On the contrary, the surface charge of the nanocapsule increases with increasing temperature. It is much more positively charged at 37 (31.6±7.1 mV) than 22° C. (9.8±4.4 mV) and even become negatively charged at 4° C. (−11.6±4.1 mV).

Pluronic F127 is an amphiphilic block copolymer with a formula PEO100-PPO65-PEO100, in which the subscripts 100 and 65 indicate the number of PEO (polyethylene oxide) and PPO (polypropylene oxide) blocks, respectively. A distinctive feature of Pluronic copolymers is that it exhibits a sol-gel transition behavior in aqueous solution when temperature increases from below to above its lower critical solution temperature (LOST) usually less than 40° C. The solution to gel transition is accompanied with a significant volume contraction as a result of dehydration of the PPO block, which is presumably responsible for the significant volume change (e.g., more than 15 times contraction from 22 to 37° C. shown in FIG. 1B) observed for the Pluronic F127 based nanocapsules synthesized in this study. This volume change has been reported to be even bigger for other Pluronic F127 based nanocapsules reported in the literature. For example, the volume contraction from ~20 to 37° C. of a Pluronic F127-PEI nanocapsule synthesized using a higher Pluronic concentration (30% w/v) and a shorter time (3 vs. 4 minutes in this study) for cross-linking between the activated Pluronic and PEI (and presumably the cross-link is weaker) was found to be more than 40 times and it is more than 1000 times for a Pluronic F127-haprin nanocapsule. The difference in the volume contraction between the PEI and heparin cross-linked Pluronic nanocapsule was attributed to the difference between the two cross-links: the latter was reported to be much more fragile and softer and hence allowing much bigger volume change. The Pluronic F127-PEI nanocapsules have been shown to have an empty core-shell like nano-reservoir structure. This observation may explain why the shrunken Pluronic F127-PEI nanocapsule (e.g., ~95 nm in this study and 100-150 nm reported in the literature is much bigger than a solid monolithic Pluronic F127 micelle in aqueous solution (~30 nm) at 37° C. The empty core of the nanocapsule was proposed to be a result of the balance between the hydrophobic interactions (leading to dehydration in the PPO blocks and volume contraction) and the repulsion between the positive charges in the cross-linked PEI molecules (resisting collapse). The increase of the nanocapsule surface charge with temperature probably is a result of the exposure of more PEI molecules on the surface in response to the volume collapse with increasing temperature. Putting together the experimental data and above discussion, a schematic representation of the nanocapsule at 22 and 37° C. can be given in FIG. 2. The empty core-shell structured nanocapsule is much smaller and more positively charged at 37 than 22° C. As will be discussed later in more detail, the temperature dependent size and surface charge and other thermally responsive properties of the nanocapsule play a key role in facilitating their uptake by mammalian cells, determining their distribution within the cells, and ultimately encapsulating trehalose for efficient intracellular delivery.

3.2. Cellular Uptake of the Nanocapsule and its Intracellular Distribution

Figure 2:
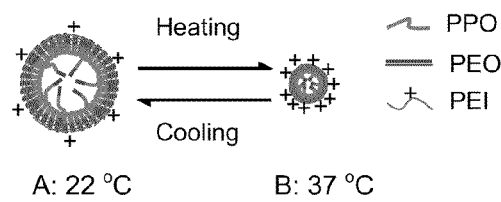
Figure 3:
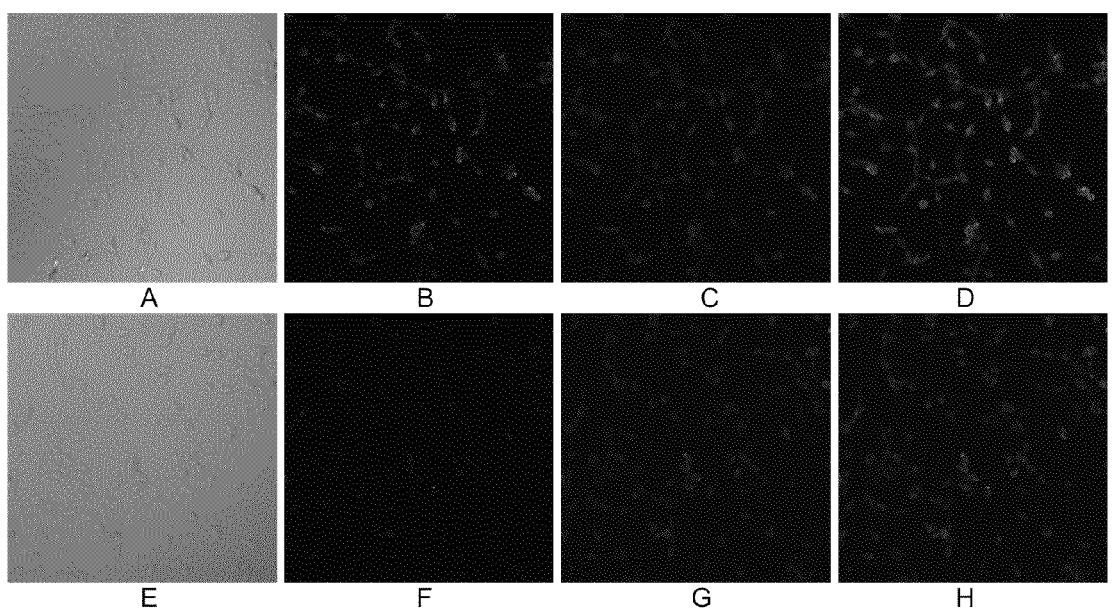
FIG. 3. Typical confocal micrographs of 3T3 fibroblasts after incubating with FITC-labeled nanocapsules in serum free culture medium containing Hoechst and LysoTracker Red under DIC contrast (A and E), green channel showing FITC-labeled nanocapsule (B and F), red channel showing the LysoTracker Red stain for endosomes/lysosomes (C and G), and the merged view of the green and red channels (D and H). The upper (A-D) and lower (E-H) panels are for cells without and with a cold shock treatment, respectively. Scale Bar: 100 μm FIG. 4. Immediate cell viability (A) and 3-day proliferation (B) of 3T3 cell after being exposed to extracellular nanocapsules at various concentrations up to 1 mg/ml followed by a 15 min cold shock at 22° C. The sample with zero nanocapsule concentration was performed to serve as control. Error bar represents standard deviation.

Typical confocal micrographs demonstrating cellular uptake of the FITC-labeled nanocapsule and its intracellular distribution are shown in FIG. 3 for cells both without (upper panels A-D) and with (lower panels E-H) a cold shock treatment at 22° C. Differential interference contrast (DIC) images of the cells (panel A and E for without and with the cold shock treatment, respectively) show the morphology of an elongated spindle which is phenotypical for 3T3 fibroblasts. Cellular uptake of the FITC-labeled nanocapsules is clearly demonstrated by the bright green fluorescence in panel B of cells without the cold shock treatment. However, the green fluorescence becomes fainted in cells with the cold shock treatment (panel F). Locations of sub-cellular organelles (mainly the endosome/lysosome) with an acidic internal environment were made visible with the fluorescent probe LysoTracker Red (red channels) in panels C and G for cells without and with the cold shock treatment, respectively. Both panel shows strong red fluorescence indicating the existence of a significant amount of endosomes/lysosomes in the cells after incubating the cells with the medium containing nanocapsules. Merged views of the green and red channels for cells without and with cold shock are shown in panels D and H, respectively. A yellowish color of the merged view in panel D indicates extensive co-staining of the two fluorescent probes (i.e., FITC and LysoTracker Red) for cells without the cold shock treatment. The yellowish color is not readily identifiable in the merged view of the red and green channels of cells with the cold shock treatment (panel H). These results indicate that the FITC-labeled nanocapsules were primarily sequestered in the endosome/lysosome system immediately after being internalized and before the cold shock treatment, suggesting endocytosis is the dominant mechanism of cellular uptake of the nanocapsules. After cold shock, however, the nanocapsules escaped the endosome/lysosome system into the cytosol (resulting in the fainted green fluorescence in Panel F), presumably by mechanically breaking the endosome/lysosome as a result of a significant volume expansion of the nanocapsule in responsive to cold shock. As shown in FIG. 1, the diameter (or volume) of the nanocapsule at 22° C. is more than 2.5 (or 15.6) times bigger than that at 37° C. (247.2±27.8 vs. 95.1±15.4 nm) and is more than 1.5 (or 3.4) time bigger than that of the endosome/lysosome (~150 nm).

The results showing in FIG. 3 clearly demonstrate the importance of thermal responsiveness of the nanocapsule for its cellular uptake and intracellular distribution. For example, the small size (~95 nm) of the nanocapsule at 37° C. is important for its cellular uptake since the nanocapsules must be small enough to be enwrapped in the clathrin coated endocytotic endosome (~150 nm) before they can be internalized by the cells via endocytosis. After internalization, the nanocapsule can mechanically break and escape the endosome/lysosome system as a result of more than 15 times volume expansion in response to a cold shock treatment at 22° C. Of note, the capability of the nanocapsule to break and escape the endosome/lysosome into the cytosol is of critical importance. This is because degradation or potentially exocytosis (if not biodegradable) of the endocytosed material as a result of their sequestration in the endosome/lysosome system has been reported to be a major bottleneck for cytosolic drug delivery via endocytosis. FIG. 3 also demonstrates that a significant amount of nanocapsules could be internalized in a short incubation period of 40 minutes, indicating an accelerated endocytosis was involved in the uptake process. The accelerated endocytosis (also called adsorptive endocytosis) is presumably attributed to the highly positively charged surface of the nanocapsule, which has a high affinity with the negatively charged cell membrane as a result of electrostatic attraction. In summary, as a result of their thermal responsiveness, the Pluronic F127-PEI nanocapsules could be easily internalized by mammalian cells and the thermal responsiveness could be further utilized to control their intracellular distribution.

3.3. Cytotoxicity of the Nanocapsule

Figure 4:
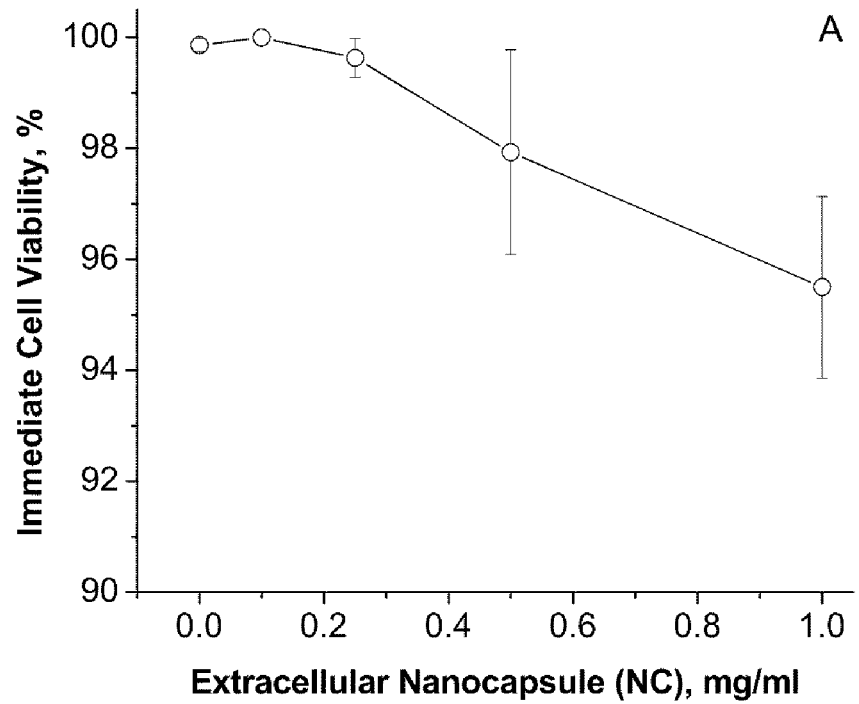
Figure 4:
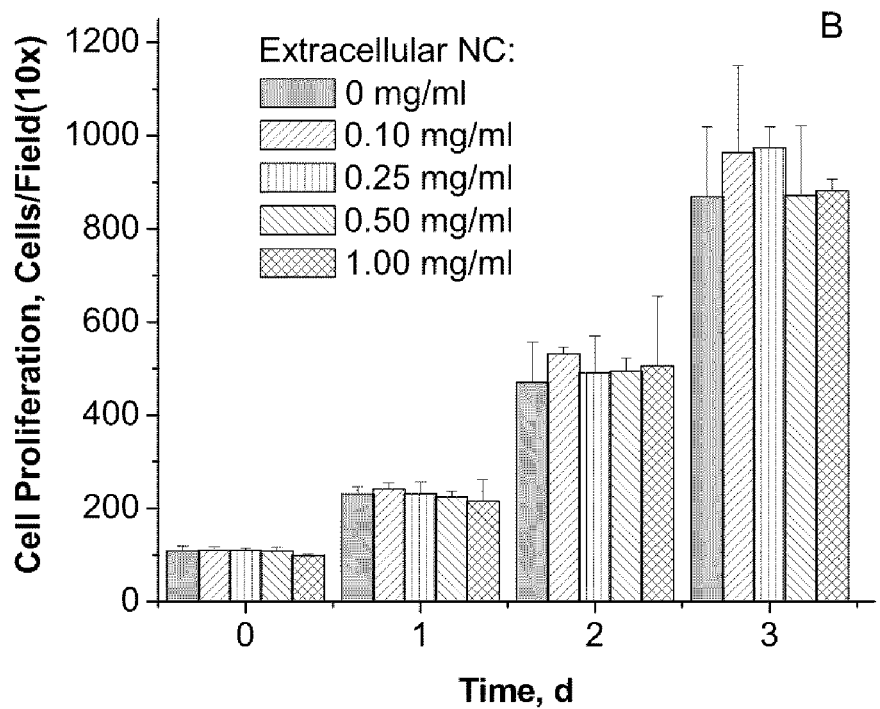

The immediate cell viability and 3-day proliferation of the 3T3 cells after being exposed to the nanocapsules (40 min at 37° C. followed by a cold shock at 22° C. for 15 min) at different extracellular concentrations from 0 to 1 mg/ml are shown in panels A and B of FIG. 4, respectively. Studies with an extracellular nanocapsule concentration of zero were performed to serve as control. FIG. 4A shows that the immediate cell viability was more than 95% under all the experimental conditions. Moreover, the 3-day proliferation of the cells exposed to nanocapsules was not significantly different from that of control. Since a significant amount of nanocapsules could be internalized by the cells during the 40 min incubation period and the nanocapsules could escape the endosome/lysosome system in response to a cold shock treatment as demonstrated in FIG. 3, the results shown in FIG. 4 (i.e., high immediate cell viability and normal proliferation in 3 days) indicate that the nanocapsules is not toxic to the cells at least under the concentration tested. Moreover, the process of breaking the endosome/lysosome by a heat shock treatment to release the nanocapsule into cytosol did not result in significant injury to the cells either.

The low cytotoxicity of Pluronic based nanocapsules has been reported in the literature and could be partially attributed to the excellent biocompatibility of its constituent polymers. Pluronic F127 has been approved by FDA (Food and Drug Administration) for use as food additives and pharmaceutical ingredients. PEI is a cationic polymer that has been commonly used for gene delivery. Although PEI could be toxic to mammalian cells at high concentrations, its cytotoxicity has been shown to be negligible when it is cross-linked with Pluronic F-127 in the nanocapsule. The high immediate cell viability and normal 3-day cell proliferation of 3T3 fibroblasts shown in FIG. 4 is consistent with this observation. Nevertheless, the intracellular trafficking of the nanocapsules released from the early endosome after cold shock may help to further explain their negligible cytotoxicity.

3.4. Nanoencapsulation and Controlled Release of Trehalose

Figure 5:
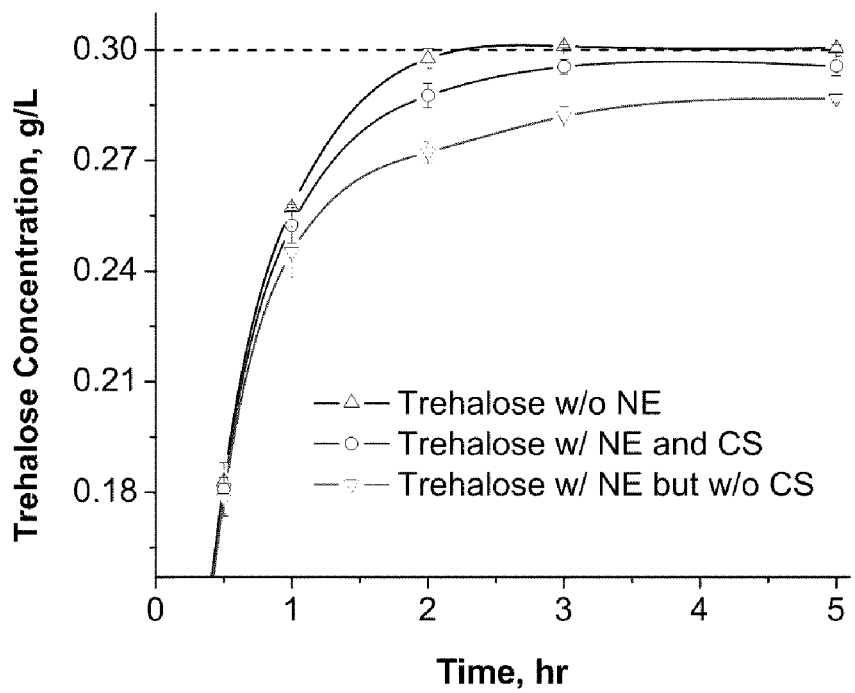
FIG. 5. Release of trehalose to 1 L deionized water at 37° C. from a dialysis bag containing 2 ml solution of 15% (w/v) dissolved trehalose without nanoencapsulation (trehalose w/o NE, Δ), mixture of dissolved and nanoencapsulated trehalose with an overall trehalose concentration of 15% (w/v) and a cold shock (CS) treatment at 22° C. before transferred to the dialysis tube (Trehalose w/NE & CS, O), and mixture of dissolved and nanoencapsulated trehalose with an overall trehalose concentration of 15% (w/v) kept at 37° C. all the time (trehalose w/NE but w/o CS, ∇). Error bar represents standard deviation.
Figure 6:
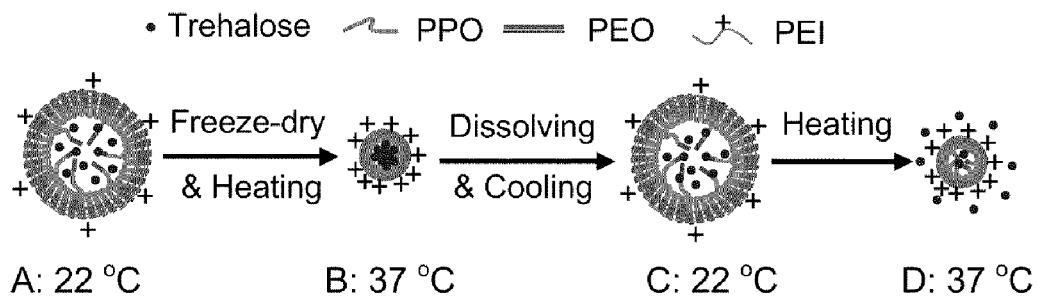
FIG. 6. A schematic representation of the process of trehalose nanoencapsulation and controlled release: Trehalose can be loaded into the nanocapsule by incubating it with aqueous trehalose solution at 22° C. (A) followed by freeze-drying and heating to 37° C. (B). A quick release of the nanoencapsulated trehalose can be achieved by cooling the trehalose nanocapsule to 22° C. (C) in aqueous solution followed by heating back to 37° C. (D).

Trehalose release patterns from the 2 ml dialysis bag into the 1 L deionized water at 37° C. under the three different experimental conditions are shown in FIG. 5. Also shown in the figure is the maximum possible trehalose concentration (i.e., 0.3 g/L represented by the horizontal dash line) in the 1 L deionized water under the equilibrium condition (i.e., the trehalose concentration outside the dialysis bag in the 1 L water is the same as that inside the dialysis bag). For the control condition with dissolved trehalose only (i.e., without nanoencapsulation), trehalose release from the dialysis bag reached equilibrium in approximately 2 hours according to the figure. For the condition with nanoencapsulation (NE) but no cold shock (CS) treatment at 22° C., however, trehalose release from the dialysis tube is apparently much slower than that under the control condition, particularly after one hour when more than 80% of the non-encapsulated trehalose was released from the dialysis tube into the 1 L deionized water in the beaker. The release was far from complete even after 5 hours for the condition with nanoencapsulation but no cold shock. Since the release of non-encapsulated trehalose from the dialysis tube reached equilibrium at 2 hr, the difference in trehalose concentration (i.e., 0.03=0.3−0.27 g/L according to the figure) in the 1 L solution outside the dialysis tube between the control and the sample with nanoencapsulation (NE) but no cold shock (CS) should be a result of trehalose nanoencapsulation in the nanocapsules. The total nanoencapsulated trehalose can then be estimated to be 0.03 g as the product of the trehalose concentration difference at 2 hr (i.e., 0.03 g/L) and the total volume of deionized water (~1 L) in the beaker. Since the total amount of empty nanocapsules used is 0.02 g (see section 2.7 in Materials and Methods), a loading capability defined as the ratio of the weight of nanoencapsulated trehalose to that of empty nanocapsule can be estimated to be 1.5 (=0.03 g trehalose/0.02 g nanocapsules). In other words, trehalose takes up approximately 60% of the total weight of the trehalose-loaded nanocapsules. These results indicate that trehalose indeed can be encapsulated in the nanocapsule by simply incubating the nanocapsule in aqueous trehalose solution at 22° C. followed by freeze drying and heating to 37° C. A schematic representation of the nanoencapsulation process is given in FIG. 6 (A→B). Interestingly, with both nanoencapsulation (NE) and a cold shock (CS) treatment at 22 for 15 min before dialysis, the trehalose release pattern is much closer to that of the control condition (i.e., without nanoencapsulation). This result indicates that the nanoencapsulated trehalose was quickly released into the 2 ml solution as a result of the cold shock treatment at 22° C. before it was transferred into the dialysis bag and the subsequent heating back to 37° C. during dialysis as schematically demonstrated in FIG. 6 (B→C→D). Based on the trehalose concentration data at 2 hr, it is estimated that approximately 75% of the total nanoencapsulated trehalose was released from the nanocapsule during the cold shock and subsequent heating process. Presumably, more nanoencapsulated trehalose can be released from the nanocapsule by a second cold shock treatment. In any event, the results given in FIG. 5 indicate that effective nanoencapsulation of trehalose in the Pluronic-PEI nanocapsule can be achieved by using a combination of incubation/freeze-drying/heating procedures. Trehalose can be withheld within the nanocapsule at 37° C. with minimum release for at least 5 hr. Moreover, an accelerated release pattern of the nanoencapsulated trehalose can be achieved by a cold shock treatment of the trehalose loaded nanocapsules at 22 for a short period of time (15 min) followed by heating back to 37° C. in aqueous solution.

Besides the thermal responsiveness of the nanocapsule in size and surface charge, the capability of the Pluronic F127-PEI nanocapsule for encapsulation and controlled release of trehalose indicates a temperature dependent wall permeability of the nanocapsule: it is high at 22° C. to allow free diffusion of trehalose in and out of the nanocapsule whereas it is so low at 37° C. that trehalose can be withheld in the nanocapsule for at least 5 hr with minimum release. In other words, it is the thermal responsiveness of the nanocapsule wall permeability that makes it possible to encapsulate the small molecular weight trehalose in the nanocapsule post its synthesis for controlled release. It has been shown that both hydrophilic and hydrophobic therapeutic agents with a molecular weight greater than 1 kDa can be effectively withheld in appropriately designed Pluronic based hydrogel or nanocapsule with minimum release for up to 2 days at a temperature above its LOST. The results from this study demonstrate that the Pluronic F127 based hydrogel nanocapsule is capable of withholding even smaller molecular weight molecules (i.e., trehalose, MW=342 Da) at 37° C. However, drugs or therapeutic agents were directly encapsulated in the hydrogel or nanocapsule during the synthesis steps in the previous studies. Successful nanoencapsulation and controlled release of drugs or therapeutic agents utilizing the temperature dependent wall permeability of the Pluronic based nanocapsule post its synthesis has never been reported until this study. This finding is significant because the direct contact between sensitive drugs or therapeutic agents and the organic solvents for nanocapsule synthesis during direct encapsulation may significantly compromise their activity, which can be avoided by the approach developed in this study utilizing the temperature dependent wall permeability of the nanocapsules. Moreover, the new approach allows the two processes of nanocapsule synthesis and drug nanoencapsulation being performed at different times, which can significantly reduce the shipping and maintenance cost. Therefore, we believe, this novel approach for nanoencapsulation opens a whole new avenue for controlled delivery of small molecular weight drugs and therapeutic agents.

3.5. Nanocapsule Assisted Intracellular Delivery of Trehalose

Figure 7:
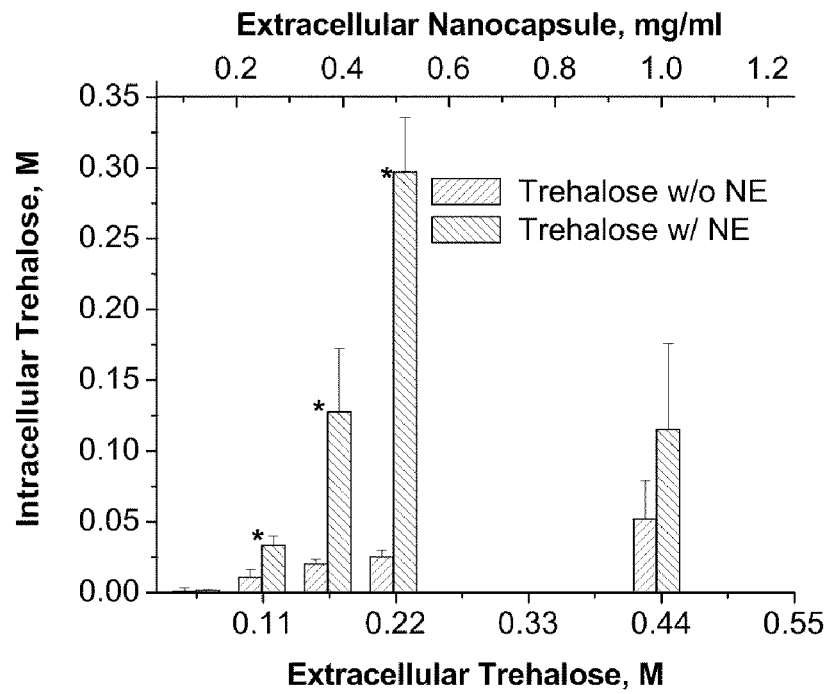
FIG. 7. Intracellular concentration of trehalose in 3T3 fibroblasts after incubating the cells in trehalose solution with both dissolved and nanoencapsulated trehalose (Trehalose w/NE) at various concentrations at 37° C. for 40 min. The sample with the same dissolved extracellular trehalose concentration but no nanoencapsulation (Trehalose w/o NE) was studied to serve as control. Error bar represents standard deviation. Asteroids indicate statistical significance.

FIG. 7 shows the intracellular trehalose concentration of 3T3 fibroblasts after incubating the cells with extracellular trehalose at 37° C. in the presence and absence of trehalose-loaded nanocapsules. The extracellular trehalose concentration for all the loading conditions is given along the bottom horizontal axis. The corresponding nanocapsule (excluding nanoencapsulated trehalose) concentration for the loading conditions with trehalose-loaded nanocapsules in the incubation medium is given along the top horizontal axis. For samples without nanocapsules, the figure shows that the measured intracellular trehalose concentration increased slightly with the extracellular trehalose concentration, but was always less than ~0.05 M under all the experimental conditions. For the samples with nanocapsules, the intracellular trehalose concentration was also negligible (<0.05 M) when the nanocapsule concentration in the extracellular medium is not higher than 0.25 mg/ml (the corresponding extracellular trehalose concentration is 0.11 M), However, when the medium nanocapsule concentration was increased to 0.375 mg/ml (the corresponding extracellular trehalose concentration is 0.165 M), the resultant intracellular trehalose concentration is significantly higher than that in the corresponding control samples without nanocapsules (0.13 vs. 0.02 M). Moreover, the intracellular trehalose concentration (~0.3 M) was even much higher than the corresponding trehalose concentration (0.22 M) in the extracellular medium when the medium nanocapsule concentration was 0.5 mg/ml. However, the intracellular trehalose concentration does not always increase with the increase of extracellular trehalose and nanocapsule concentration. When the extracellular nanocapsule concentration was 1 mg/ml (the corresponding extracellular trehalose was 0.44 M), the intracellular trehalose concentration was measured to be only ~0.12 M with big variation and is not significantly different from that of control. This result probably is because of the high concentration of extracellular trehalose (0.44 M) used that results in significant damage to the cells (or more specifically, their plasma membrane), since a significant amount of cells were observed to detach from the substrate during washing after the loading step. If the cell membrane is comprised, the cells cannot withhold trehalose during washing and a low intracellular trehalose concentration is assured. In summary, intracellular delivery of a significant amount of trehalose into mammalian cells sufficient for biostabilization of mammalian cells (0.1-0.3 M) is achievable with the aid of the Pluronic F127-PEI nanocapsules. Nevertheless, the extracellular trehalose and nanocapsule concentrations should be carefully controlled.

Figure 8:
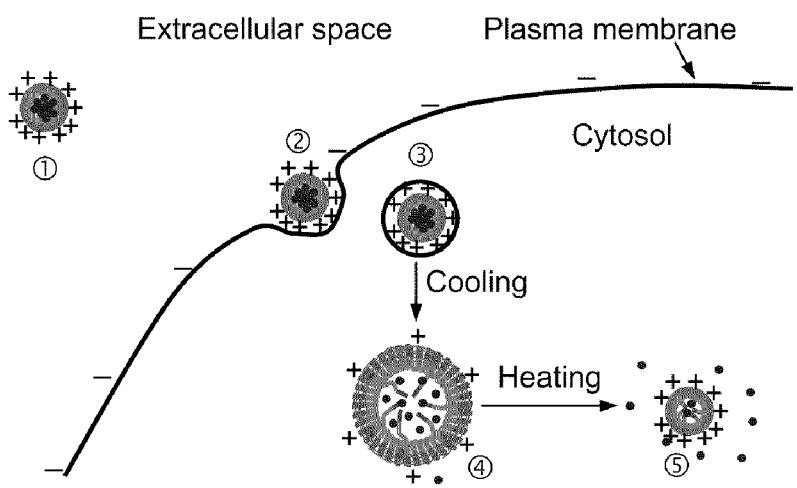
FIG. 8. A schematic representation of the process of nanocapsule assisted intracellular delivery of trehalose: The positively charged trehalose-loaded nanocapsule floating in culture medium at 37° C. (1) is attracted onto the negatively charged plasma membrane and enwrapped in a clathrin-coated pit on the plasma membrane (2). The coated pit then buds into the cytoplasm to form the early endosome (~150 nm in size, 3). A cold shock treatment at 22° C. results in breaking the early endosome by the swollen nanocapsule to release trehalose into the cytosol slowly by passive diffusion (4). A quick release of the nanoencapsulated trehalose can be achieved by heating the cells back to 37° C. to squeeze the dissolved trehalose out of the nanocapsule as a result of the more than 15 times of volume contraction (5).

The data in FIG. 7 clearly demonstrates that a significant amount of trehalose could be internalized by 3T3 fibroblasts in a short incubation period of 40 minutes with an appropriate amount of extracellular trehalose and trehalose-loaded nanocapsules. However, cellular uptake of trehalose dissolved in solution by fluid phase endocytosis (or pinocytosis) has been shown to be much less effective. For example, it has been shown that more than 5 hours and even days are required for platelets and human mesenchymal stem cells to uptake even a much smaller amount of trehalose (<~0.05 M) by pinocytosis. Our results from the control samples are consistent with this observation in the literature. The high efficiency of trehalose uptake by the 3T3 fibroblasts in the presence of the Pluronic F127-PEI nanocapsules is presumably due to two reasons: 1), the positively charged surface of the nanocapsule results in an accelerated endocytotic (i.e., adsorptive endocytosis discussed previously) pathway rather than that of the slow fluid phase endocytosis; and 2), the high trehalose encapsulation capability of the nanocapsule results in a much higher amount of trehalose being enwrapped in each endosome comparing with pinocytosis for which the contents in the endosome is dominantly water. Based on the discussions here and previously in Section 3.2, a schematic representation of the nanocapsule assisted trehalose loading process is proposed in FIG. 8. The highly positively charged trehalose-loaded nanocapsule floating in culture medium at 37° C. (1) is attracted onto the negatively charged plasma membrane and enwrapped in a clathrin-coated pit on the plasma membrane (2). The coated pit then buds into the cytoplasm to form the early endosome (~150 nm in size, (3)). A cold shock treatment at 22° C. results in breaking the early endosome by the swollen nanocapsule to release trehalose into the cytoplasm slowly by diffusion (4). A quick release of the encapsulated trehalose can be achieved by heating the cells back to 37° C. to squeeze the dissolved trehalose out of the nanocapsule as a result of the more than 15 times of volume contraction (5).

Figure 9:
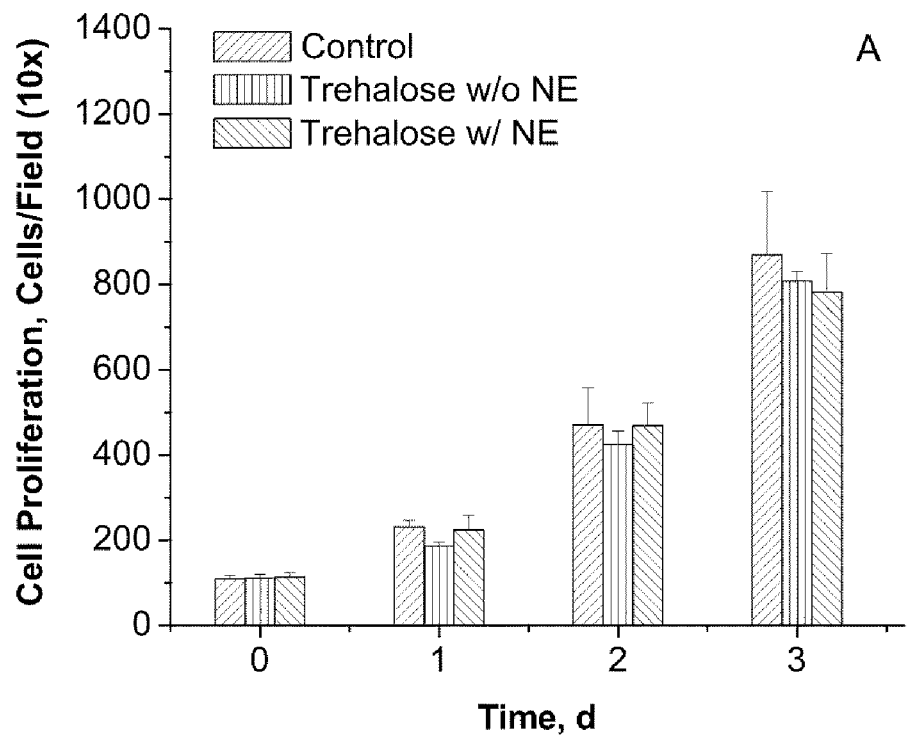
FIG. 9. Cell proliferation (A) and collagen production (B) in 3 days of 3T3 fibroblasts in culture after incubating the cells for 40 minutes in fresh medium without trehalose (Control), medium containing 0.22 M dissolved trehalose without nanoencapsulation (Trehalose w/o NE), and medium containing 0.22 M both dissolved and nanoencapsulated trehalose using 0.5 mg/ml nanocapsules (i.e., the condition for delivering ~0.3 M intracellular trehalose in FIG. 7, Trehalose w/NE). Error bar represents standard deviation.
Figure 9:
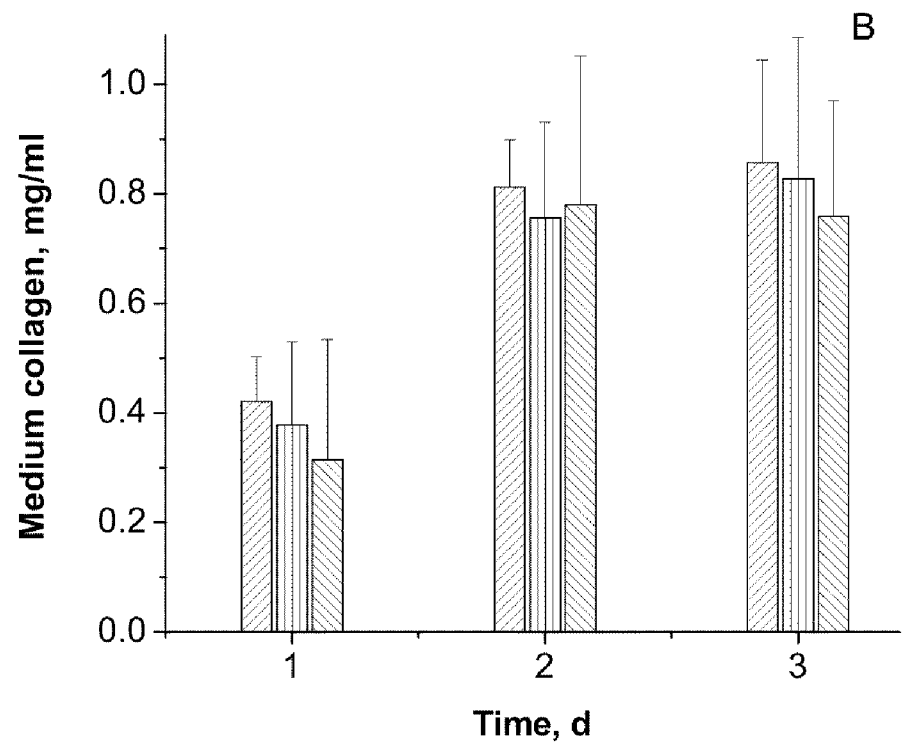

3.6. Immediate Cell Viability, Proliferation, and Collagen Production of Trehalose Loaded Cells The immediate cell viability was measured to be 96.8±1.6% after loading the cells with trehalose under the condition that results in ~0.3 M intracellular trehalose according to FIG. 7. The 3 day cell proliferation and collagen production data of fresh control cells (Control), cells exposed to extracellular trehalose without nanoencapsulated trehalose (Trehalose w/o NE), and cells loaded with ~0.3 M intracellular trehalose (Trehalose w/NE) are shown in panels A and B of FIG. 9, respectively. No significant differences are observable between the three groups in terms of both cell proliferation and collagen production. Therefore, the 3T3 cells can survive well and function normally after being loaded with exogenous trehalose at least when the intracellular trehalose concentration is not higher than 0.3 M.

Although a significant amount of intracellular trehalose might result in apparent osmotic stress on the cells, it is not surprising to observe that 3T3 fibroblasts can survive well after being loaded with 0.3 M intracellular trehalose. This is because a variety of sensitive mammalian cells including hepatocytes and renal cells have been reported to be capable of controlling its volume under osmotic stress by activating a regulatory volume control mechanism. Moreover, trehalose should not interrupt the biochemical processes in cells in view of its non-reducing nature. No evidence is better to support these arguments than the fact that even the osmotically sensitive mammalian oocytes have been shown to survive well after microinjection with 0.15 M intracellular trehalose. Trehalose was observed to be eliminated rapidly from the cells during their embryonic development. Moreover, the trehalose loaded oocytes were found to survive well post cryopreservation using trehalose as the sole cryoprotectant. Further studies are ongoing in our lab to cryo- and lyo-preserve the NIH 3T3 fibroblasts loaded with 0.1-0.3 M trehalose.

4. Summary and Conclusions

In this study, thermally responsive Pluronic F127-PEI nanocapsules were synthesized and characterized. They have a small size (~95 nm in diameter), positively charged surface, and low wall permeability at 37° C. whereas they are larger (>~250 nm in diameter), neutral to negatively charged and highly permeable at or below 22° C. It was shown that a significant amount of the nanocapsules can be easily internalized by fibroblasts in 40 min at 37° C. via absorptive endocytosis, a much faster endocytotic pathway in comparison to fluid phase endocytosis that is normally used by cells for self-feeding. This is because the positively charged nanocapsules have a high affinity with the negatively charged cell membrane presumably as a result of electrostatic interaction. In addition, the small size (~95 nm) of the nanocapsule at 37° C. allows them being easily entrapped in endosomes (~150 nm) during endocytosis. It was further demonstrated that the nanocapsules can mechanically break and escape the endosome/lysosome system into cytosol in response to a cold shock treatment at or below room temperature when their diameter is more than ~250 nm (more than 1.5 times greater than that of the early endosome, ~150 nm). Results from immediate cell viability and long-term cell proliferation studies indicate that the nanocapsules are not toxic to mammalian cells at the dose used for intracellular delivery of trehalose. Trehalose can be loaded into the nanocapsules by simply incubating the nanocapsules with trehalose in water at room temperature when the permeability of the nanocapsule wall is high followed by freeze-drying to remove water. It was further found trehalose can be withheld in the nanocapsule dissolved in aqueous solution for hours at 37° C. when the nanocapsule wall permeability is low. A quick release of the nanoencapsulated trehalose can be achieved by thermally cycling the trehalose-loaded nanocapsules between 22 and 37° C. Moreover, a significant amount of trehalose (up to 0.3 M) can be loaded into the cytosol of NIH 3T3 fibroblasts by a short (40 min) incubation of the trehalose loaded nanocapsules with the cells at 37° C. followed by a short (20 min) cold shock treatment at or below room temperature. An intracellular trehalose concentration of 0.1-0.3 M is generally believed to be sufficient to protect mammalian cells from damage under the stress of both cryo and lyopreservation. Therefore, loading trehalose into mammalian cells using the thermally responsive nanocapsules should provide an enabling approach to achieve long-term stabilization of important mammalian cells for future use particularly at ambient temperatures, which is critical to the eventual success of modern cell-based medicine.

EXAMPLE 2

Activation of Pluronic F127 and Preparation of Pluronic F127-Chitosan Nanocapsules 6.3 g Pluronic F 127 and 122.17 mg 4-dimethylaminopyridine (DMAP) were dissolved in 15 ml anhydride 1,4-dioxane solution with 139 µl triethylamine (TEA). After stirring for 30 min under N2 atmosphere, 125 mg succinic anhydride in anhydride 5 ml 1,4-dioxane was added dropwisely. The mixture was stirred under N2 atmosphere for 24 h at room temperature. Then the solvent was removed with a rotary evaporator and the residue was filtered and precipitated in ice-cold diethyl ether for three times. Finally, the precipitate was dried under vacuum overnight to get the white powder of di-carboxylated Pluronic F127.

The thermally responsive Pluronic F127-chitosan nanocapsule was prepared using a modified emulsification/solvent evaporation method. 100 mg carboxylated Pluronic F127 and 5 mg 1-Ethyl-3-[3-dimethylaminopropyl] carbodiimide hydrochloride (EDC) were dissolved in 1 ml CH2Cl2 for 15 minutes. The solution was added drop-wise into 10 ml aqueous solution of chitosan oligosaccharide (7.5 mg/ml) with a pH of 5. The oil-in-water mixture was emulsified for 4 min using a Branson 450 Sonifier (Danbury, Conn.). Then the solution was stirred gently for 24 hours. Organic solvents in the emulsion were then removed by evaporation using a rotary evaporator until the solution became clear. The sample was then dialyzed against DI water with a Spectra/Por (Spectrum Labs, Rancho Dominguez, Calif.) dialysis tube (MWCO, 50 kD).

Figure 10:
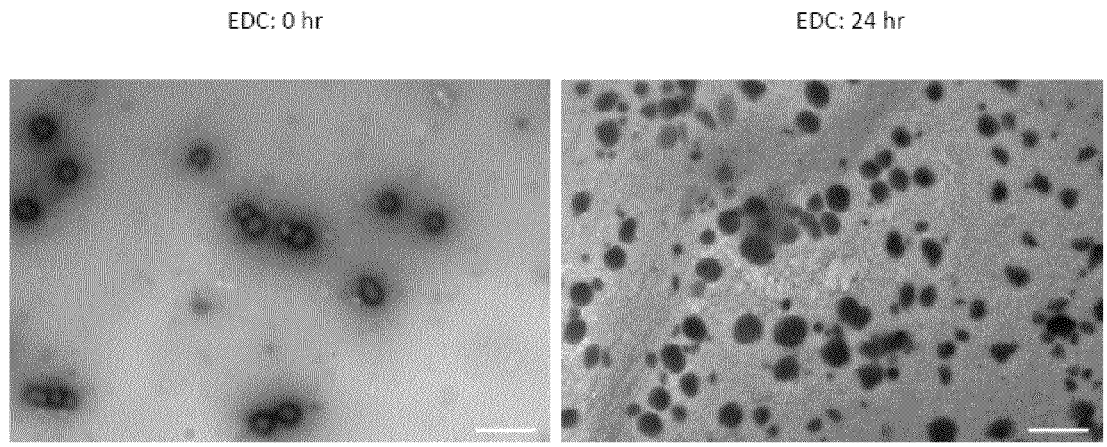
FIG. 10. TEM images of nanocapsules in accordance with certain aspects of the present disclosure.

Characterization of Nanocapsule Morphology, Size, Surface Charge and Pluronic/Chitosan Ratio in the Nanocapsule The morphology of the synthesized nanocapsules was studied using transmission electron microscopy (TEM). For TEM analysis, one drop (2 μl) of the aqueous nanocapsule solution (2 mg/ml) was dried on a copper TEM grid for 10 min. The dried nanocapsule specimen was then stained by adding a drop (~2 μl) of 2% (w/v) uranyl acetate solution followed by drying for 10 min. The sample was then examined using a Hitachi H-800 transmission electron microscope. All the procedures were performed at room temperature. Typical TEM images of the nanocapsules are shown in FIG. 10. The empty-core shell structure is clearly visible if no EDC was used as the catalyst (EDC: 0 hr) while the shell was thickened and tightened after 24 hr EDC catalysis and the empty core-shell structure is not clear anymore.

Figure 11:
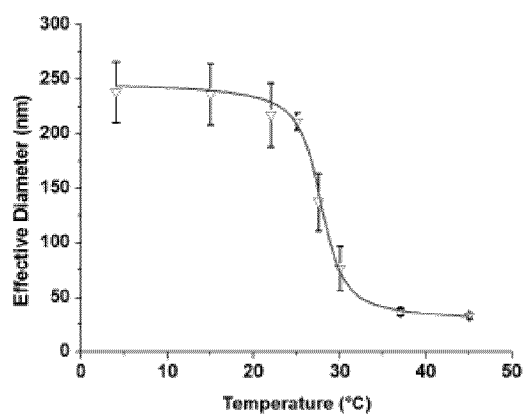
FIG. 11. Thermal responsiveness of a nanocapsule in accordance with certain aspects of the present disclosure is illustrated.
Figure 11:
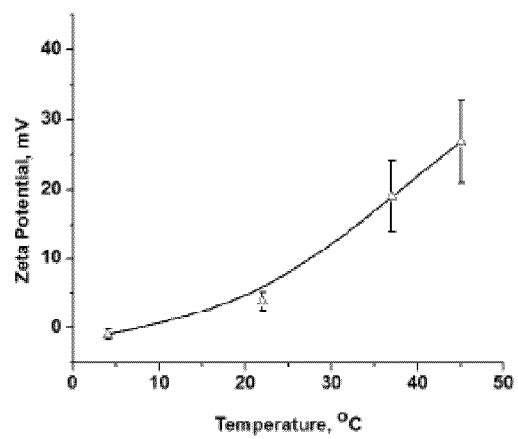

The size (FIG. 11, top panel) and surface charge (FIG. 11 bottom panel, represented by the surface $\zeta$ potential) of the synthesized nanocapsule at various temperatures from 4-45° C. was further measured using a Wyatt dynamic light scattering (Santa Barbara, Calif.) and Brookhaven Zeta potential analyzer (Holtsville, N.Y.) respectively, for which the nanocapsule was dissolved in 1x phosphate-buffered saline (PBS) at a concentration of 1 mg/ml. The data in FIG. 11 clearly shows the thermal responsiveness of the nanocapsule in both size and surface charge.

Figure 12:
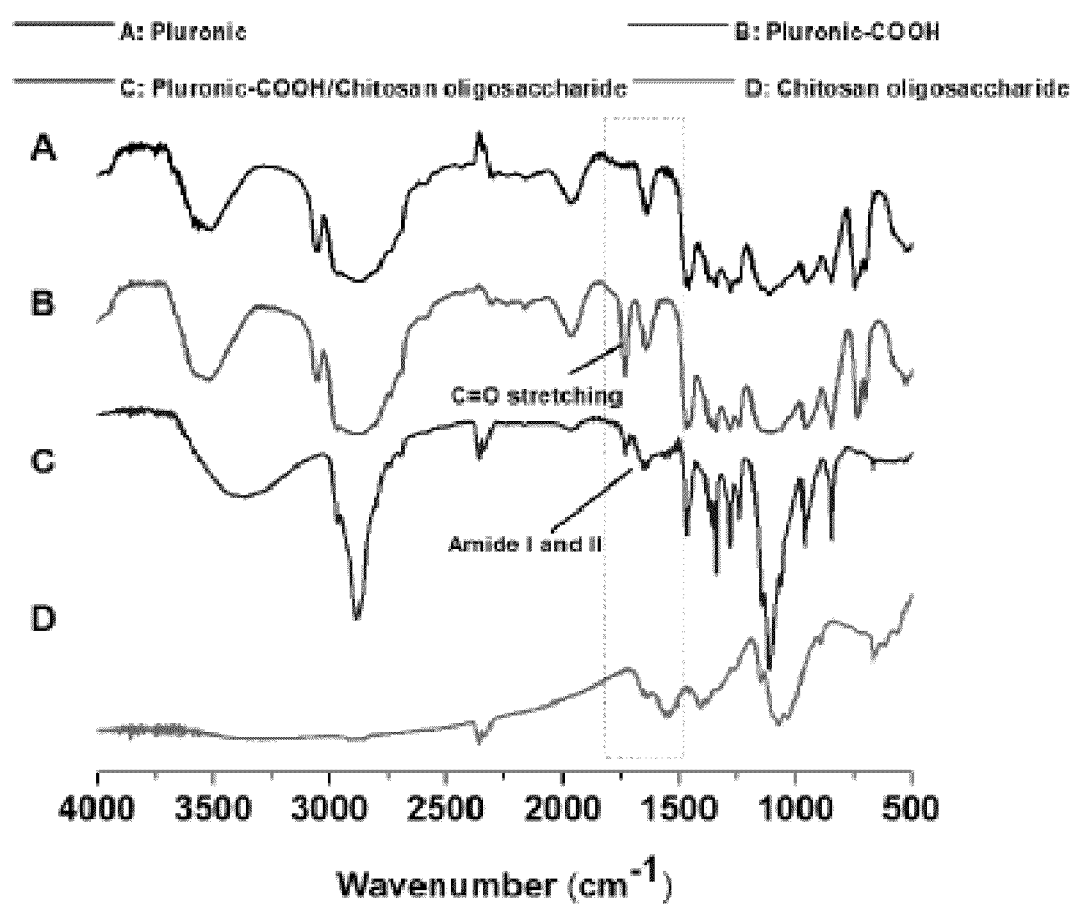
FIG. 12. Activation of the Pluronic 127 and the crosslinking reaction between the Pluronic F127 and chitosan results in the formation of the Pluronic F127-chitosan nanocapsule.

FT-IR was used to characterize the polymer structure. $CH_2Cl_2$ was used to dissolve the polymer or help form a suspension. The samples were tested at room temperature with $CH_2Cl_2$ as control and the spectrums were recorded and further processed using OrignPro software. The FTIR data shown in FIG. 12 clearly indicates the activation of the Pluronic 127 and the crosslinking reaction between the Pluronic F127 and chitosan that results in the formation of the Pluronic F127-chitosan nanocapsule.

Cytotoxicity of the Synthesized Pluronic F127-Chitosan Nanocapsules

Immediate cell viability, long-term cell proliferation and cell differentiation were studied to test the cytotoxicity of the nanocapsules synthesized. For immediate cell viability study (i.e., short-term toxicity), C3H10T1/2 and MCF-7 cells were seeded in 33 mm Petri dishes at a density of $2.5 \times 10^5$ and $5 \times 10^5$ cells/dish in 1 ml medium respectively. After 24 h, the cell culture medium was replaced with warm (37° C.) serum-free medium containing nanocapsules of various concentrations. After incubating for 40 min at 37° C., cells were washed three times using warm (37° C.) 1x PBS to remove any extracellular nanocapsules followed by a cold shock treatment in fresh culture medium for 15 min at 22° C. Cell viability of the cells immediately after cold shock was determined using the standard live/dead assay kit purchased from Invitrogen. The cells were examined using an Olympus BX 51 microscope equipped with fluorescent cubes and a QICAM CCD digital camera (QImaging, Surrey, BC, Canada). At least 10 representative images were taken and processed using the Linksys 32 software (Linkam, UK) to count viable (green fluorescence) and dead (red fluorescence) cells. Immediate cell viability was calculated as the ratio of the number of viable cells to the total number of cells, which were at least 1200 for each sample.

For long-term cell proliferation studies, C3H10T1/2 and MCF-7 cells were seeded in 33 mm Petri dishes at a relatively low density of $0.5 \times 10^5$ and $1 \times 10^5$ cells/dish in 1 ml medium respectively. At 24 h, the cells were exposed to nanocapsules in the same way as that described above for immediate cell viability studies. After cold shock, the cells were further cultured for 3 days to monitor their proliferation (long-term toxicity). This was done by taking at least 10 representative images of the samples every day including the day (taken as day 0) when the cells were exposed to nanocapsules. The total number of cells in each image were counted using NIH ImageJ.

Figure 13:
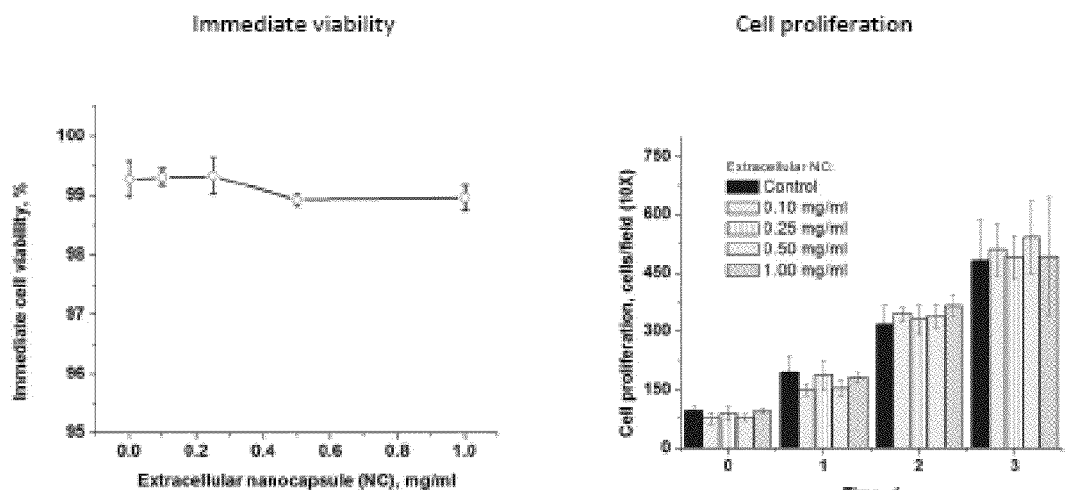
FIG. 13. Cellular uptake of a nanocapsule in accordance with the present disclosure does not appear to affect the immediate and long-term survival of cells.
Figure 13:
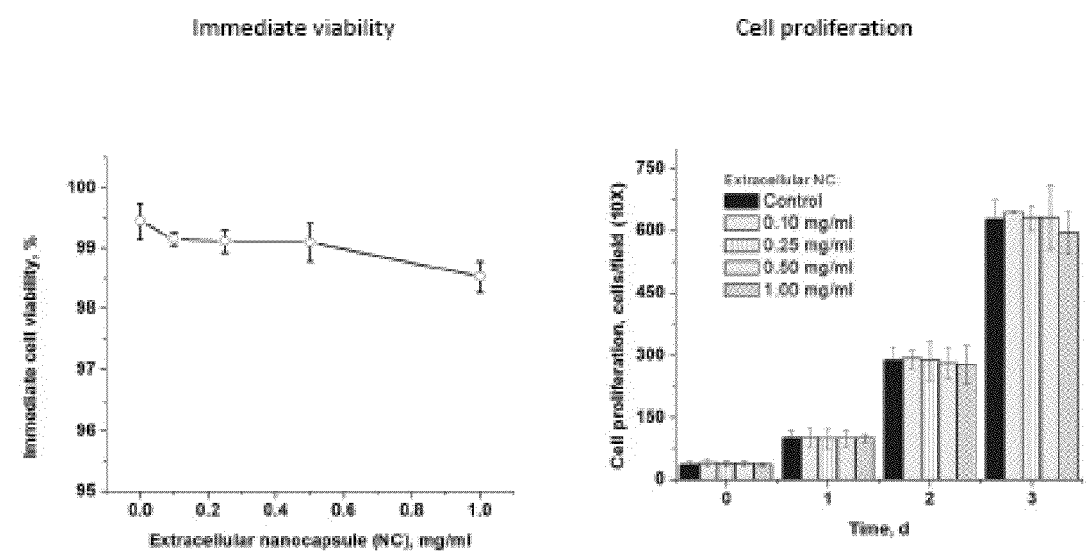

The results of immediate viability and cell proliferation are shown in FIG. 13. Cellular uptake of the nanocapsule doesn't appear to affect the immediate and long-term survival of the cells.

For adipogenic differentiation study, C3H10T1/2 cells were seeded in 33 mm Petri dishes at a relatively low density of $2.5 \times 10^5$ cells/dish in 1 ml medium. At 24 h, the cells were exposed to nanocapsules in the same way as that described above for immediate cell viability studies. After cold shock, the cells were further cultured for 2 days before inducing adipogenic differentiation. Three days later, change the adipogenic induction medium to maintenance medium by completely replacing the spent induction medium. Two days later, change the medium back to induction medium. The adipogenic induction medium consisted of DMEM high glucose supplemented with 1 mM dexamethasone, 0.2 mM indomethacin, 0.01 mg/ml insulin, 0.5 mM 3-isobutyl-1-methyl-xanthine, and 10% FCS. The adipogenic maintenance medium was composed of DMEM high glucose with 0.01 mg/ml insulin and 10% FCS. Adipogenic potential was assessed by Oil Red O staining. The cells were washed with PBS and fixed with 4% paraformaldehyde for 30 min at room temperature after 4 cycle induction/maintenance. Then the cells were washed with 60% isopropanol and incubated with filtered 0.3% Oil Red O (Sigma-Aldrich, St. Louis, Mo.) in 60% isopropanol for 30 min. After one wash in 60% isopropanol and three washes in PBS, images of the cells were taken.

Figure 14:
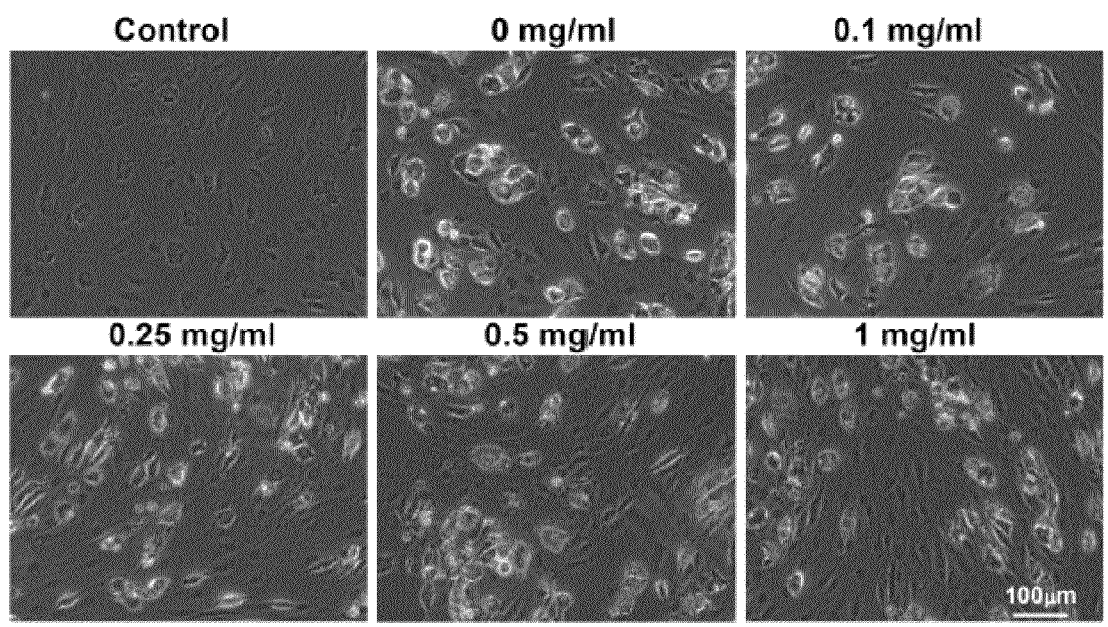
FIG. 14. Cellular uptake of a nanocapsule in accordance with the present disclosure does not appear to significantly affect the capability of adipogenic differentiation of cells.

The results are shown in FIG. 14 and cellular uptake of the nanocapsule does not appear to significantly affect the capability of adipogenic differentiation of the cells.

Cellular Uptake and Intracellular Distribution of the Nanocapsule

To study cellular uptake and the subsequent intracellular distribution of the Pluronic F127-chitosan nanocapsules, nanocapsules were first labeled with the fluorescent probe FITC. A total of 30 mg of the freeze-dried nanocapsules was dissolved in 2.3 ml of 0.1 M sodium carbonate buffer at pH 9, followed by adding dropwise a total of 110 μl of 26 mM FITC solution (in DMSO). FITC labeling of the nanocapsules was done by allowing the solutions to react for 8 h at 4° C. under gentle and continuous shaking in the dark. A total of 6.1 mg ammonium chloride was then added into the solution for 2 h at 4° C. to quench the reaction. The FITC labeled nanocapsules were further purified by dialysis against deionized water in the dark for 24 hours with the water being replaced every 3-5 hours.

To study cellular uptake of the FITC labeled nanocapsules, MCF-7 cells were seeded in 33 mm Petri dishes at a density of $5 \times 10^5$ cells/dish in 1 ml medium. After 24 h, the culture medium was replaced with serum-free medium containing FITC-labeled nanocapsules (500 μg/ml) and LysoTracker Red DND-99 (55 nM). The latter is a fluorescent probe that can permeate cell plasma membrane and accumulates in subcellular organelles with an acidic internal environment such as the endosome and lysosome. After incubation for 40 min at 37° C., cells were washed three times using warm 1x phosphate-buffered saline (PBS). The cells were then fixed using 4% warm paraformaldehyde with 5 μg/ml Hoechst 33342 for 20 min either immediately or after a cold shock treatment by incubating the cells in 1x PBS for 15 min at 22° C. After fixation, the cells were washed using 1x PBS and intracellular distribution of FITC-labeled nanocapsules in the cells was examined using a confocal microscope (LSM 510, Carl-Zeiss Inc, Oberkochen, Germany) with fluorescent capability.

Figure 15:
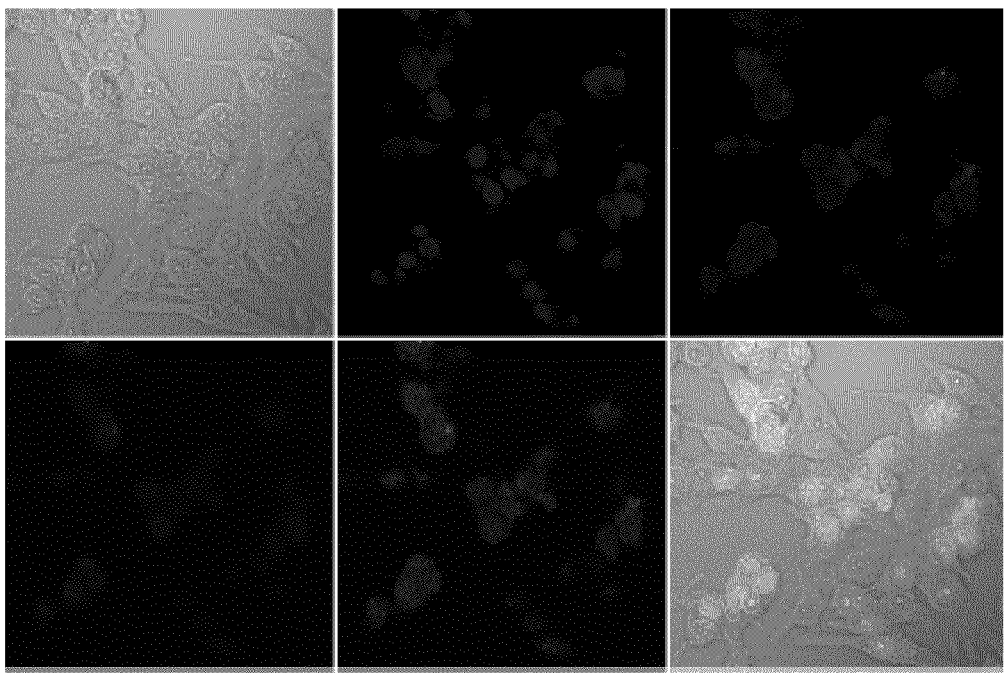
FIG. 15. Confocal images showing cell uptake of the labeled nanocapsule.
Figure 15:
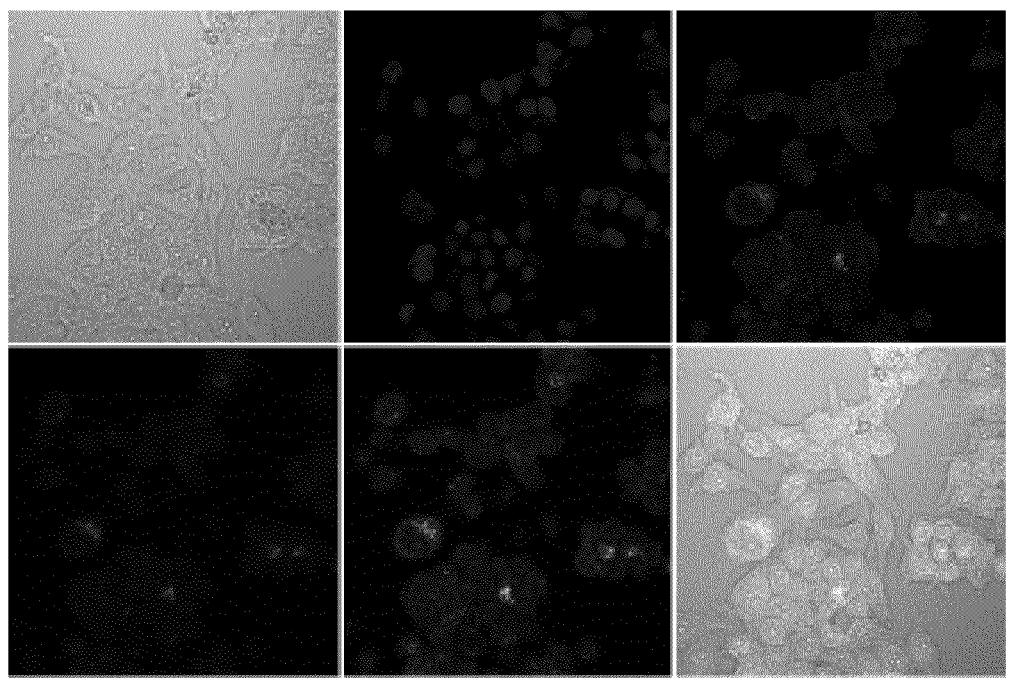
Figure 16A:
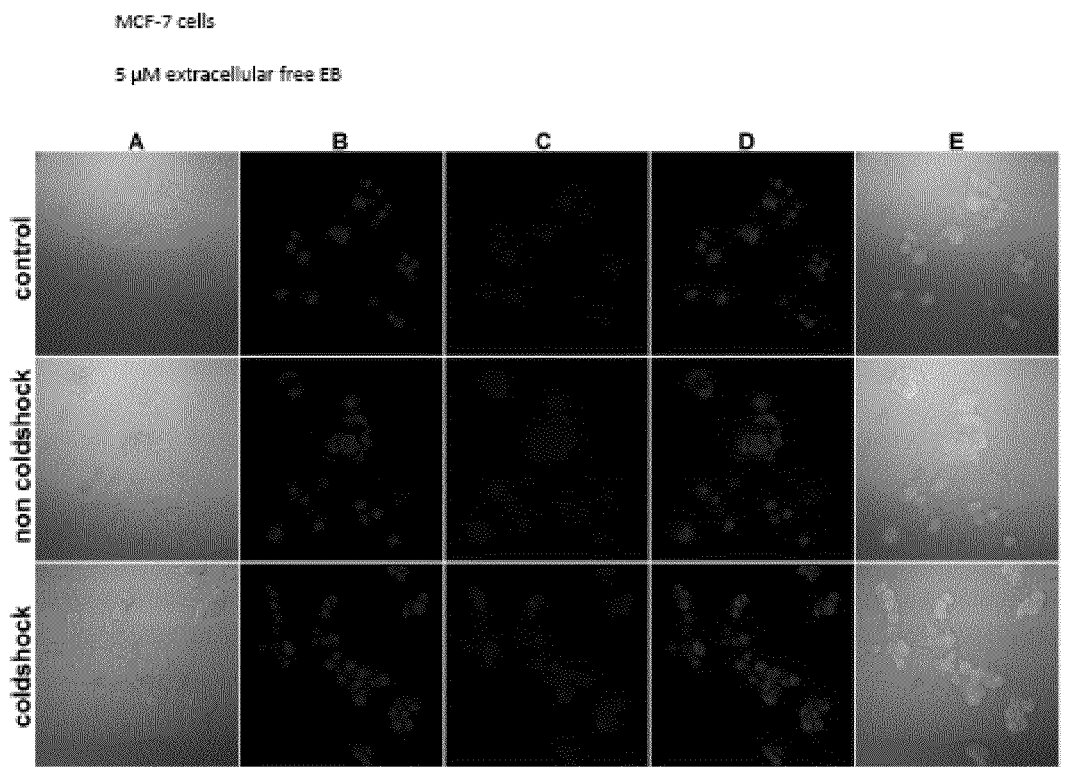
FIG. 16. Cellular uptake of the encapsulated EB either in the presence or absence of free extracellular EB.
Figure 16B:
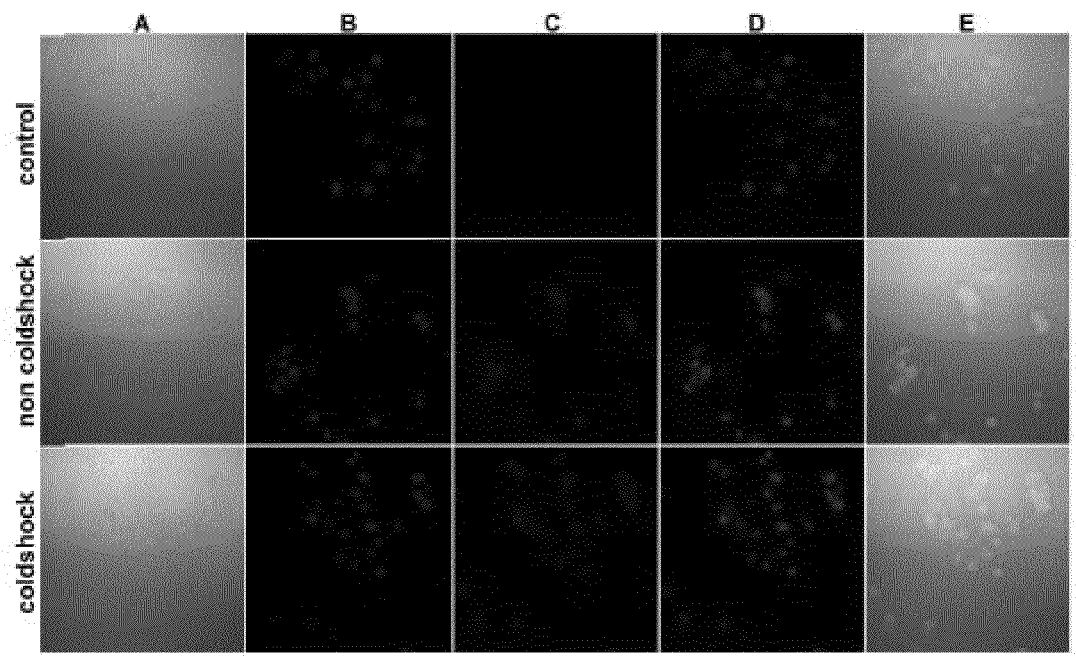
Figure 16C:
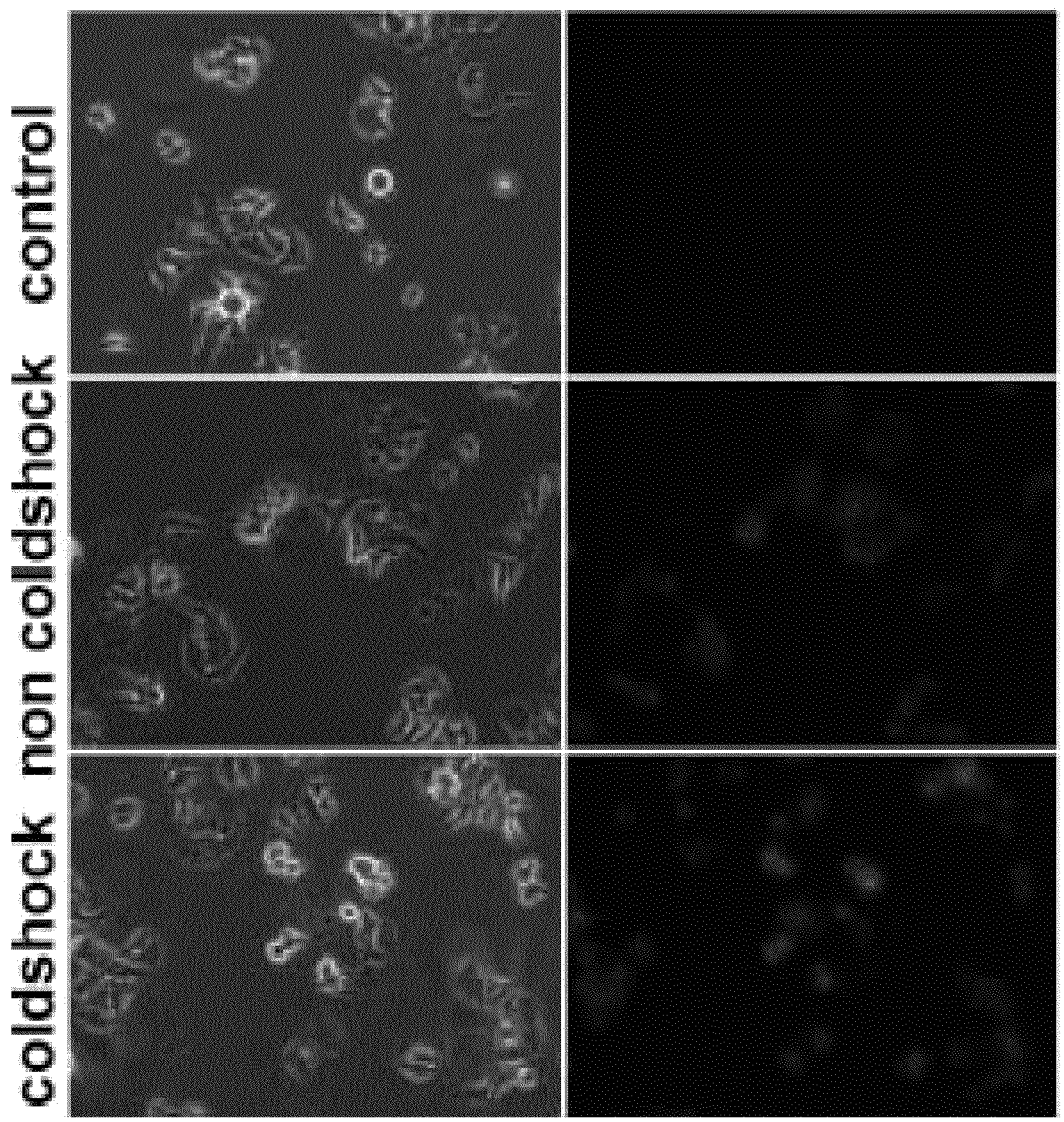
Figure 16D:
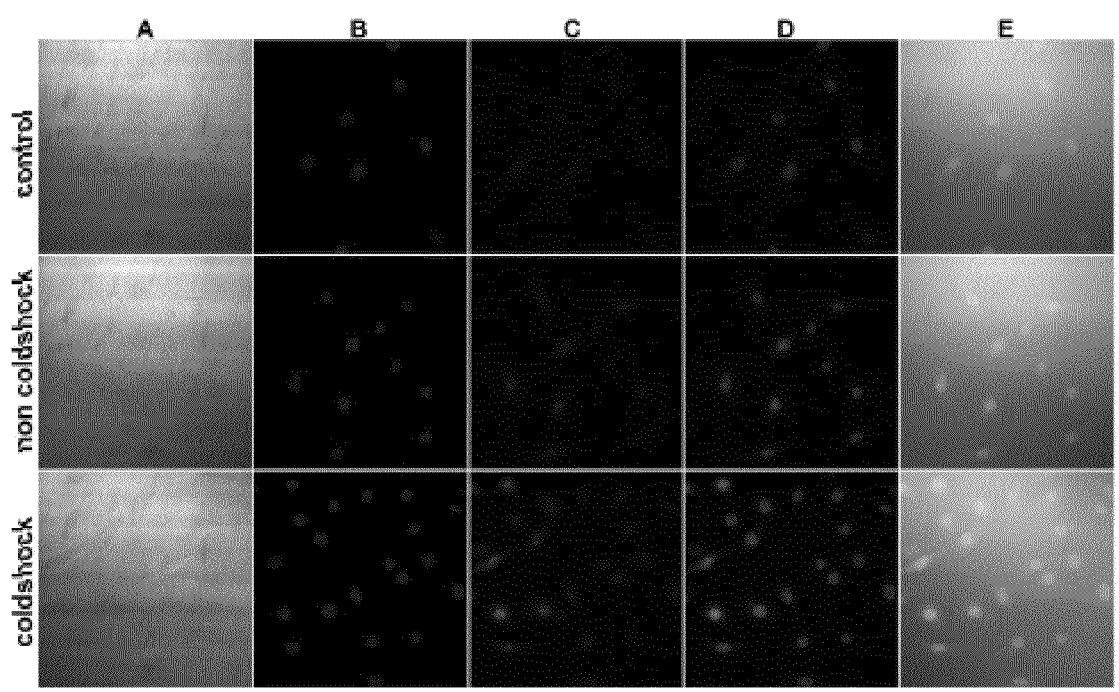
Figure 16E:
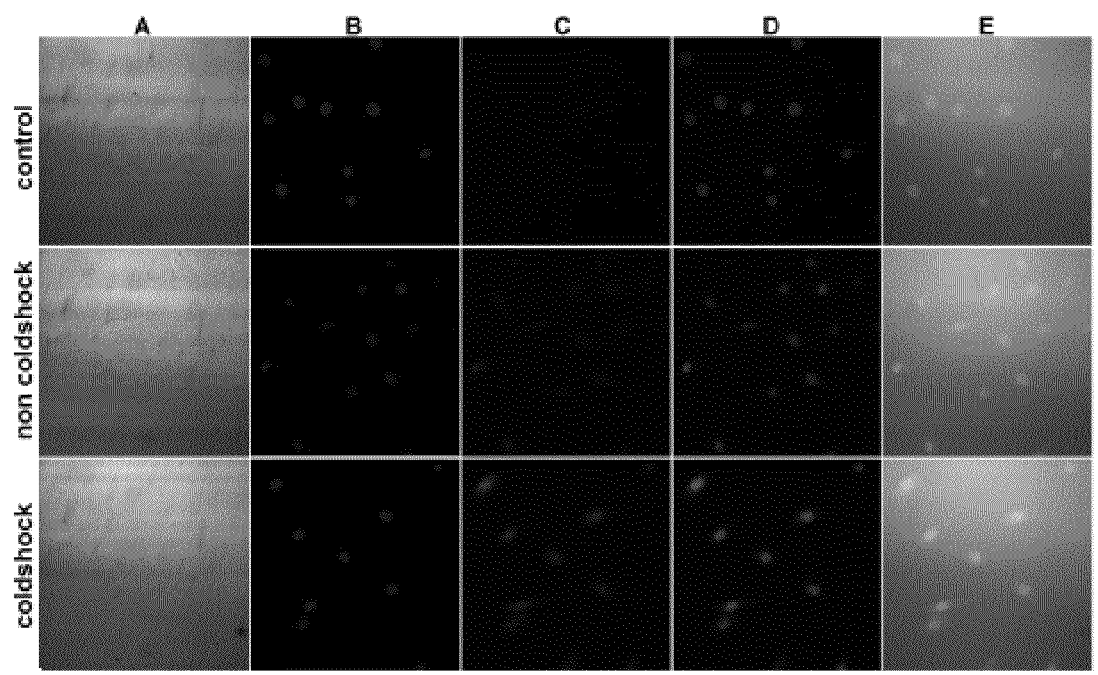

Confocal images show cell uptake of the labeled nanocapsule as illustrated in FIG. 15. Without cold shock treatment, the nanocapsule co-located with the early endosome (yellowish spotted appearance) while with cold shock, co-localization of the nanocapsule and early endosome is not clearly visible.

Encapsulation and Intracellular Delivery of Fluorescence Dye

Encapsulation of fluorescence dye, ethidium bromide (EB), was done in two steps: 1), incubating the nanocapsules (7.5 mg/ml) with EB (150 μM final concentration) in water overnight (~12 hr) at 4° C. when the nanocapsules were swollen and their wall permeability was high; and 2), freeze-drying the sample to remove water both inside and outside the nanocapsules. EB, which diffused into the nanocapsule during the incubating step, should remain in the nanocapsule after freeze drying. For the samples with the step of removing free EB, high EB concentration, 10 mg/ml, was used. After incubating at 4° C. over night and freeze drying, the samples were dissolved in 37° C. DI water. And the free EB was removed during dialysis process at 37° C. for 5 hours with one time change of dialysis water.

For intracellular delivery of EB, the freeze-dried mixture of EB and EB-loaded nanocapsules or EB-loaded nanocapsules (after removing of free EB) were preheated to 37° C. and dissolved in warm (37° C.) serum-free culture medium. The procedures performed for cellular uptake of the EB loaded nanocapsules was the same as that used for the uptake of empty nanocapsules. After cold shock at 22° C. for 15 min, the cells were further incubated for 30 minutes for dye fully release.

Figure 17:
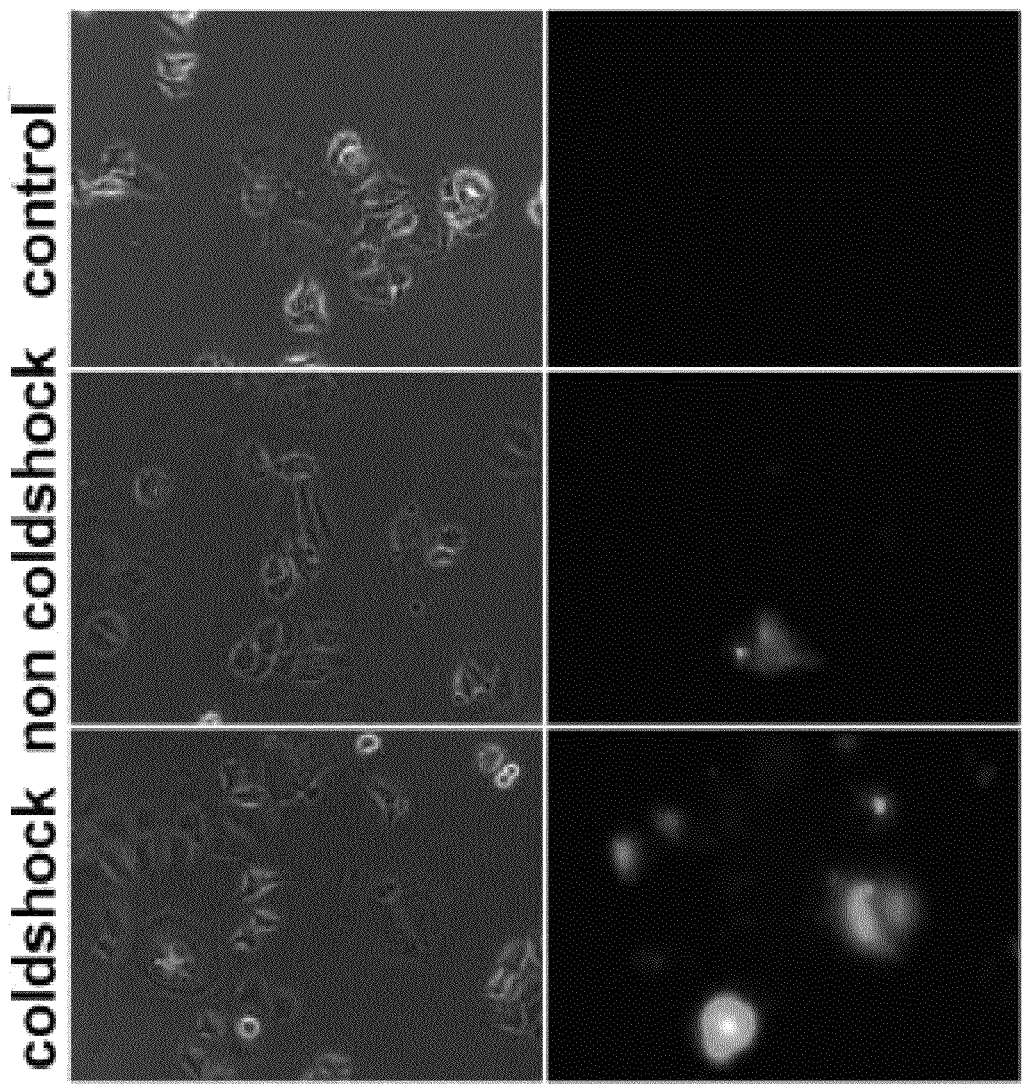
FIG. 17. Shows that a nanocapsule in accordance with the present disclosure can be used to condense DNA plasmids to transfect cells and a cold shock treatment can significantly enhance the transfection efficiency.

Cellular uptake of the encapsulated EB either in the presence or absence of free extracellular EB is shown in FIGS. 16A-E. All the data show that the nanocapsule can be used to encapsulate the dye and facilitate its uptake by MCF-7 and C3H10T1/2 cells. Moreover, cold shock treatment can be used to control the release of the dye so that they can bind with chromosome in the nucleus to give brighter red fluorescence.

eGFP Plasmid Transfection using Pluronic/PEI Nanocapsules 16.4 μl eGFP plasmid (0.46 mg/ml) was complexed with 50 μl nanocapsules (1 mg/ml) at an N/P ratio of about 45 at 37° C. for 1 hour. MCF-7 cells were seeded in 33 mm Petri dishes at a density of $2\times10^5$ cells/dish in 1 ml medium. After 24 h, the culture medium was replaced with serum-free medium containing eGFP plasmid/nanocapsules complexs with a final nanocapsule concentration of 0.5 mg/ml. After incubation for 5 hours at 37° C., cells were washed three times using warm 1x phosphate-buffered saline (PBS). The cells were then cultured for 48 hours or after a cold shock treatment by incubating the cells in 1x PBS for 15 min at 22° C. After fixation, the cells were washed using 1x PBS and was examined using a fluorescence microscope to check the GFP expression. The data in FIG. 17 clearly shows that the nanocapsule can be used to condense DNA plasmids to transfect cells and a cold shock treatment can significantly enhance the transfection efficiency.

What is claimed:

1. A method for intracellular delivery of small molecules comprising:
   encapsulation said small molecules in said thermally responsive nanocapsule comprising a polymeric hydrogel nanoparticle by decreasing the temperature of the nanocapsule to increase the permeability of the nanocapsule, such that the small molecules are sucked into or diffuse into the nanocapsule;
   delivering the nanocapsule into a cell by increasing the temperature of the nanocapsule; and
   releasing the small molecules from the nanocapsule into the cell.

2. The method of claim 1, wherein the nanocapsule comprises a polycation comprising polyethylenimine.

3. The method of claim 1, wherein the nanocapsule has a diameter of less than 150 nm at a temperature of greater than 35° C.

4. The method of claim 1, wherein the nanocapsule has a diameter of greater than 150 nm at a temperature of less than 25° C.

5. The method of claim 1, wherein the temperature is decreased to less than about 25° C.

6. The method of claim 1, wherein the temperature is increased to greater than about 35° C.

7. The method of claim 1, wherein the nanocapsule is delivered into the cell by endocytosis and is located in an endosome of the cell.

8. The method of claim 7, further comprising decreasing the nanocapsule temperature after it is delivered into the cell, thereby increasing the diameter of the nanocapsule so as to cause damage to the endosome of the cell whereby the nanocapsule is released into the cytosol of the cell.

9. The method of claim 1, further comprising further increasing the nanocapsule temperature after it is delivered into the cell, thereby decreasing the diameter of the nanocapsule whereby the small molecules are squeezed out of the nanocapsule into the cell.

10. The method of claim 1, further comprising decreasing the nanocapsule temperature after it is delivered into the cell, thereby increasing the permeability of the nanocapsule whereby the small molecules diffuse out of the nanocapsule into the cell.

11. The method of claim 1, wherein the small molecule comprises a DNA plasmid, siRNA, microRNA, or combinations thereof.

* * * * *

UNITED STATES PATENT AND TRADEMARK OFFICE
CERTIFICATE OF CORRECTION

| | | |
|---|---|---|
| PATENT NO. | : 8,318,207 B2 | Page 1 of 1 |
| APPLICATION NO. | : 12/705072 | |
| DATED | : November 27, 2012 | |
| INVENTOR(S) | : He | |

It is certified that error appears in the above-identified patent and that said Letters Patent is hereby corrected as shown below:

In the Claims

Column 20, line 11, as a new line following "comprising:", please insert --providing small molecules and a thermally responsive nanocapsule comprising a polymer hydrogel nanoparticle--.

Column 20, line 12, "encapsulation of" should be changed to "encapsulating said".

Signed and Sealed this
Seventh Day of October, 2014

Michelle K. Lee
*Deputy Director of the United States Patent and Trademark Office*